(12) United States Patent
Muraoka et al.

(10) Patent No.: US 6,420,381 B1
(45) Date of Patent: Jul. 16, 2002

(54) NAPHTHYRIDINE DERIVATIVES

(75) Inventors: Masami Muraoka, Toyonaka; Hitoshi Ban, Nishinomiya; Naohito Ohashi, Takatsuki, all of (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/762,599

(22) PCT Filed: Aug. 5, 1999

(86) PCT No.: PCT/JP99/04257

§ 371 (c)(1),
(2), (4) Date: Feb. 9, 2001

(87) PCT Pub. No.: WO00/09505

PCT Pub. Date: Feb. 24, 2000

(30) Foreign Application Priority Data

Aug. 11, 1998 (JP) .............................. 10-226685

(51) Int. Cl.⁷ ....................... A61K 31/45; C07D 471/04
(52) U.S. Cl. ....................... 514/300; 546/122
(58) Field of Search .................. 546/122; 514/303

(56) References Cited

U.S. PATENT DOCUMENTS 6,300,500 B1    10/2001   Muraoka et al. ............ 546/122

FOREIGN PATENT DOCUMENTS

| EP | 0842933 | 5/1998 |
| EP | 0947515 | 10/1999 |
| WO | A9638445 | 12/1996 |
| WO | A9823615 | 6/1998 |

OTHER PUBLICATIONS

Tanaka et al., J. Med. Chem., vol. 41, pp. 4408–4420, (1998).

*Primary Examiner*—Bernard Dentz
(74) *Attorney, Agent, or Firm*—Birch, Stewart, Kolasch & Birch, LLP

(57) ABSTRACT

A compound of the formula (I):

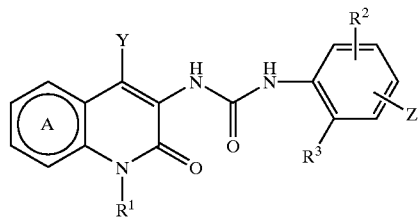

wherein Ring A is substituted or unsubstituted pyridine ring, Y is substituted or unsubstituted alkyl, etc., $R^1$ is hydrogen, or substituted or unsubstituted alkyl, etc., $R^2$ is hydrogen or lower alkyl, $R^3$ is lower alkyl, Z is 1) $-D^1-Q$ [$D^1$ is direct bond or divalent $C_{1-8}$ hydrocarbon, etc., Q is hydroxy, carboxyl, etc.], or 2) $-D^2M-E-W$ [$D^2$ is direct bond or divalent $C_{1-8}$ hydrocarbon, etc., M is oxygen, sulfur, etc., E is direct bond or divalent $C_{1-8}$ hydrocarbon, etc., W is hydroxyl, carboxyl, etc.], or a prodrug thereof, or a pharmaceutically acceptable salt of the same, which exhibits acyl-CoA: cholesterol acyl transferase (ACAT) inhibitory activity, and is useful as an agent for treatment of hyperlipidemia and atherosclerosis.

8 Claims, No Drawings

NAPHTHYRIDINE DERIVATIVES

This application is the national phase under 35 U.S.C. §371 of PCT International Application No. PCT/JP99/04257 which has an International filing date of Aug. 5, 1999, which designated the United States of America.

TECHNICAL FIELD

The present invention relates to a compound, a prodrug thereof, or a pharmaceutically acceptable salt of the same, which exhibits acyl-CoA: cholesterol acyl transferase (ACAT) inhibitory activity, and is useful as an agent for treatment of hyperlipidemia and atherosclerosis, and a use thereof.

PRIOR ART

Cerebral vessel disorders such as stroke and myocardial infarction, which rank in high in causes of death in developed countries, break out with being accompanied by atherosclerosis as basal disease. From the results of epidemiology research, it is pointed out that hypercholesterolemia is one of risk factors for atherosclerosis, and there are mainly used anti-hyperlipidemic agents, which can reduce cholesterol level in blood, in the prophylaxis or treatment thereof. However, there is no sufficiently effective agent in terms of the efficacy thereof. Recently, it is observed that cells derived from macrophage accumulate cholesterol ester droplet within the cells and become foam cells in atherosclerotic lesions, and it is clarified that these foam cells deeply participate in the developments of atherosclerotic lesions (Arteriosclerosis, 10, 164–177, 1990). In addition, it is reported that ACAT activity is increased and cholesterol esters are accumulated in the vascular wall of atherosclerotic lesions (Biochem. Biophys. Acta, 617, 458–471, 1980). Therefore, an inhibitor of ACAT, which catalyses cholesterol esterification, is expected to suppress the formation or the development of atherosclerotic lesions as a result of the inhibition of foam cell formation and of cholesterol; ester accumulation in lesions.

On the other hand, cholesterol in food is absorbed in the free form at intestinal epidermal cells, and then released in the form of chylomicron esterified by ACAT into the blood. Therefore, an inhibitor of ACAT is expected to reduce the cholesterol level in the blood by the inhibition of absorption of cholesterol in food at the intestine and of reabsorption of cholesterol released into the intestine (J. Lipid. Research, 34, 279–294, 1993).

JP-A-9-48780 discloses a naphthyridine derivative having an ACAT inhibitory activity. Some of the compounds of the present invention are included within the scope of said patent publication, but said publication never discloses concretely those compounds in Examples, etc.

DISCLOSURE OF INVENTION

An object of the present invention is to provide a compound having an ACAT inhibitory activity and being useful as an agent for treatment of hyperlipidemia and atherosclerosis.

The present inventors have intensively studied in order to solve the above-mentioned problems, and have found that a compound of the following formula (1) or (51), a prodrug thereof, and a pharmaceutically acceptable salt of the same (hereinafter, referred to as "the present compound") exhibits a potent ACAT inhibitory activity, and have accomplished the present invention. That is, the present invention relates to the following:

[1] A compound of the formula (I):

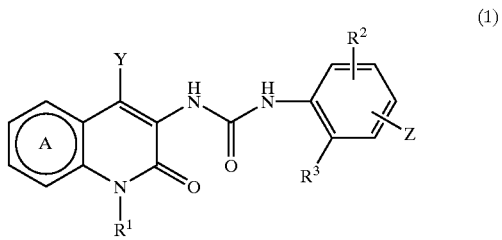

wherein Ring A is a substituted or unsubstituted pyridine ring,

Y is a substituted or unsubstituted alkyl group, a substituted or unsubstituted cycloalkyl group, or a substituted or unsubstituted aromatic group, $R^1$ is a hydrogen atom, a substituted or unsubstituted alkyl group, a substituted or unsubstituted alkenyl group, a substituted or unsubstituted alkynyl group, or a substituted or unsubstituted cycloalkyl group, $R^2$ is a hydrogen atom or a lower alkyl group, $R^3$ is a lower alkyl group, Z is 1) —$D^1$—Q wherein $D^1$ is a direct bond or a divalent hydrocarbon group having 1 to 8 carbon atoms and optionally containing an unsaturated bond, Q is a hydroxy group, a carboxyl group, a substituted or unsubstituted heteroaryl group, or a group of the formula: —$NR^4R^5$ ($R^4$ and $R^5$ are independently a hydrogen atom, a lower alkoxy-substituted or unsubstituted lower alkyl group, a cycloalkyl group, or an aralkyl group, or $R^4$ and $R^5$ may combine each other, and with the adjacent nitrogen atom to which they bond, form a saturated cyclic amino group having 4 to 8 carbon atoms as ones forming the said ring, and optionally having one —$NR^8$— ($R^8$ is a hydrogen atom, a substituted or unsubstituted lower alkyl group, a substituted or unsubstituted phenyl group, a substituted or unsubstituted benzyl group, or a lower alkoxycarbonyl group) or one oxygen atom in the cycle thereof), provided that when Q is a substituted or unsubstituted heteroaryl group, then $D^1$ is not a direct bond, or 2) —$D^2$—M—W wherein $D^2$ is a direct bond or a divalent hydrocarbon group having 1 to 8 carbon atoms and optionally containing an unsaturated bond, M is an oxygen atom, a sulfur atom, a sulfinyl group or a sulfonyl group, or a group of the formula: —NHC(=O)—, —C(=O)NH— or —$NR^6$— ($R^6$ is a hydrogen atom or a lower alkyl group), E is a direct bond or a divalent hydrocarbon group having 1 to 8 carbon atoms and optionally containing an unsaturated bond, W is a hydroxyl group, a carboxyl group, a substituted or unsubstituted heteroaryl group, or a group of the formula: —$NR^4R^5$ ($R^4$ and $R^5$ are as defined above), provided that when W is a hydroxy group, a carboxyl group or a group of the formula: —$NR^4R^5$, then E is not a direct bond, or a prodrug thereof, or a pharmaceutically acceptable salt of the same;

[2] The compound according to the above [1], or a prodrug thereof, or a pharmaceutically acceptable salt of the same, wherein Ring A is oneof the groups of the following formulae (a), (b) and (c).

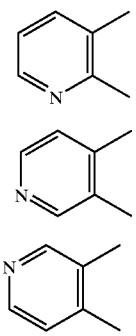

(a)
(b)
(c)

[3] The compound according to the above [2], or a prodrug thereof, or a pharmaceutically acceptable salt of the same, wherein Y is a substituted or unsubstituted aromatic group.

[4] The compound according to the above [3], or a prodrug thereof, or a pharmaceutically acceptable salt of the same, wherein $R^1$ is a substituted or unsubstituted alkyl group, or a substituted or unsubstituted alkenyl group.

[5] The compound according to the above [4], or a prodrug thereof, or a pharmaceutically acceptable salt of the same, wherein Ring A is an unsubstituted pyridine ring.

[6] The compound according to the above [5], or a prodrug thereof, or a pharmaceutically acceptable salt of the same, wherein Y is a phenyl group being substituted by a lower al,yl group or a lower alkoxy group, or a pyridyl group being substituted by a lower alkyl group or a lower alkoxy group.

[7] The compound according to the above [6], or a prodrug thereof, or a pharmaceutically acceptable salt of the same, wherein Z is a group of the formula: —$D^1$—Q, $D^1$ is a divalent hydrocarbon group having 1 to 4 carbon atoms, Q is a hydroxy group, a substituted or unsubstituted heteroaryl group, or a group of the formula: —$NR^4R^5$.

[8] The compound according to the above [6], or a prodrug thereof, or a pharmaceutically acceptable salt of the same, wherein Z is a group of the formula: —$D^1$—Q, $D^1$ is a methylene group or an ethylene group, Q is a hydroxy group, a substituted or unsubstituted heteroaryl group, or a group of the formula: —$NR^4R^5$ ($R^4$ and $R^5$ are independently a lower alkyl group, or $R^4$ and $R^5$ may combine each other, and with the adjacent nitrogen atom to which they. bond, form a saturated cyclic amino group having 5 or 6 atoms as ones forming the said ring, and optionally having one —$NR^8$— ($R^8$ is a hydrogen atom, a lower alkyl group, a phenyl group, a lower alkoxycarbonyl group, or a benzyl group) or one oxygen atom in the cycle thereof.

[9] The compound according to the above [5] or [6], or a prodrug thereof, or a pharmaceutically acceptable salt of the same, wherein Z is a hydroxymethyl group, (1-pyrazolyl)methyl group, 2-(1-pyrazolyl)ethyl group, (3,5-dimethyl-1-pyrazolyl)methyl group, (1-imidazolyl) methyl group, 2-(1-imidazolyl)ethyl group, (2-methyl-1-imidazolyl)methyl group, (1,2,4-triazol-1-yl)methyl group, 2-(1,2,4-triazol-1-yl)ethyl group, (1-piperidinyl) methyl group, (1-pyrrolidinyl)methyl group, (4-methyl-1-piperazinyl)methyl group, morpholinomethyl group, diethylaminomethyl group or dipropylaminomethyl group.

[10] The compound according to the above [6], or a prodrug thereof, or a pharmaceutically acceptable salt of the same, wherein Z is a group of the formula: —$D^2$—M—E—W, $D^2$ is a direct bond or a divalent hydrocarbon group having 1 to 4 carbon atoms, M is an oxygen atom, or a group of the formula: —NHC(=O)—, —C(=O)NH— or —$NR^6$—, E is a divalent hydrocarbon group having 1 to 4 carbon atoms, W is a hydroxy group, a carboxyl group, a substituted or unsubstituted heteroaryl group, or a group of the formula: —$NR^4R^5$.

[11] The compound according to the above [6], or a prodrug thereof, or a pharmaceutically acceptable salt of the same, wherein Z is a group of the formula: —$D^2$—M—E—W, $D^2$ is a direct bond, a methylene group, or an ethylene group, M is an oxygen atom, or a group of the formula: —NHC(=O)—, —C(=O)NH— or —$NR^6$—, E is a divalent hydrocarbon group having 1 to 4 carbon atoms, W is a hydroxy group, a subsituted or unsubstituted heteroaryl group, or a group of the formula: —$NR^4R^5$ ($R^4$ and $R^5$ are independently a lower alkyl group, or $R^4$ and $R^5$ may combine each other, and with the adjacent nitrogen atom to which they bond, form a saturated cyclic amino group having 5 or 6 atoms as ones forming the said ring, and optionally having one —$NR^8$— ($R^8$ is a hydrogen atom, a lower alkyl group, a phenyl group, a lower alkoxycarbonyl group, or a benzyl group) or one oxygen atom in the cycle thereof.

[12] The compound according to the above [6], or a prodrug thereof, or a pharmaceutically acceptable salt of the same, wherein Z is a group of the formula: —$D^2$—M—E—W, $D^2$ is a direct bond, a methylene group, or an ethylene group, M is a group of the formula: —NHC(=O)— or —C(=O)NH—.

[13] The compound according to the above [6], or a prodrug thereof, or a pharmaceutically acceptable salt of the same, wherein Z is (2-pyridyl)-methoxy group, 2-(2-pyridyl) ethoxy group, (3-pyridyl)methoxy group, 2-(3-pyridyl) ethoxy group, (4-pyridyl)methoxy group, 2-(4-pyridyl) ethoxy group, 2-(1,2,4-triazol-1-yl)ethoxy group, 3-(1,2,4-triazol-1-yl)propoxy group, 2-(diethylamino)ethoxy group, 3-(diethylamino)propoxy group, 2-(1-piperidinyl) ethoxy group, 3-(1-piperidinyl)propoxy group, 2-(morpholino)ethoxy group, 3-(morpholino)propoxy group, (2-pyridyl)-methoxymethyl group, (3-pyridyl) methoxymethyl group, (4-pyridyl)-methoxymethyl group, {3-(1,2,4-triazol-1-yl)propoxy}methyl group, (2-pyridyl)methylaminomethyl group, (3-pyridyl) methylaminomethyl group, (4-pyridyl) methylaminomethyl group, {N-(2-pyridyl)methyl-N-methyl}-aminomethyl group, {N-(3-pyridyl)methyl-N-methyl}aminomethyl group, or {N-(4-pyridyl) methyl-N-methyl)aminomethyl group.

[14] The compound according to the above [6], or a prodrug thereof, or a pharmaceutically acceptable salt of the same, wherein $R^2$ is a hydrogen atom, and $R^3$ is an isopropyl group or a tert-butyl group.

[15] The compound according to the above [6], or a prodrug thereof, or a pharmaceutically acceptable salt of the same, wherein $R^2$ and $R^3$ are an isopropyl group.

[16] The compound according to the above [9], or a prodrug thereof, or a pharmaceutically acceptable salt of the same, wherein $R^2$ is a hydrogen atom, and $R^3$ is an isopropyl group or a tert-butyl group.

[17] The compound according to the above [13], or a prodrug thereof, or a pharmaceutically acceptable salt of the same, wherein $R^2$ and $R^3$ are an isopropyl group.

[18] The compound according to the above [4], or a prodrug thereof, or a pharmaceutically acceptable salt of the same, wherein Z is a group of the formula: —$D^1$—Q, $D^1$ is a direct bond, and Q is a hydroxy group or a group of the formula: —$NR^4R^5$.

[19] The compound according to the above [18], or a prodrug thereof, or a pharmaceutically acceptable salt of the same, wherein Y is a phenyl group being substituted by a group of the formula: —$M^1$—$E^1$—T ($M^1$ is a direct bond, an oxygen atom, a sulfur atom, or a group of the formula: —$NR^{61}$— ($R^{61}$ is a hydrogen atom or a lower alkyl group), $E^1$ is a divalent hydrocarbon group having 1 to 8 carbon atoms and optionally containing an unsaturated bond, and T is a hydroxy group, a halogen atom, a carboxyl group, a lower alkoxycarbonyl group, a benzyloxy-carbonyl group, a cyano group, a benzyloxy group, a lower alkoxy group, a lower alkanoyloxy group, a lower alkylthio group, a lower alkylsulfinyl group, a lower alkylsulfonyl group, a methanesulfonyloxy group, an alkyl-substituted or unsubstituted benzenesulfonyloxy group, a lower alkanoylamino group, a lower alkoxycarbonylamino group, a lower alkylsulfonamido group, a phthalimido group, a substituted or unsubstituted heteroaryl group, or a group of the formula: —$NR^{41}R^{51}$ ($R^{41}$ and $R^{51}$ are independently a hydrogen atom, a lower alkoxy-substituted or unsubstituted lower alkyl group, a cycloalkyl group, a lower alkoxycarbonyl group, or an aralkyl group, or $R^{41}$ and $R^{51}$ may combine each other, and with the adjacent nitrogen atom to which they bond, form a saturated cyclic amino group having 4 to 8 carbon atoms as ones forming the said ring, and optionally having one —$NR^{81}$— ($R^{81}$ is a hydrogen atom, a substituted or unsubstituted lower alkyl group, a substituted or unsubstituted phenyl group, a substituted or unsubstituted benzyl group, or a lower alkoxycarbonyl group) or one oxygen atom in the cycle thereof), or a. group of the formula: —C(=O)$NR^{41}R^{51}$ ($R^{41}$ and $R^{51}$ are as defined above)).

[20] The compound according to the above [19], or a prodrug thereof, or a pharmaceutically acceptable salt of the same, wherein $M^1$ is an oxygen atom, $E^1$ is a hydrocarbon group having 2 to 4 carbon atoms, and T is a hydroxy group or a group of the formula: —$NR^{41}R^{51}$.

[21] The compound according to any one of the above [1] to [20], or a prodrug thereof, or a pharmaceutically acceptable salt of the same, which is a compound of the formula (51):

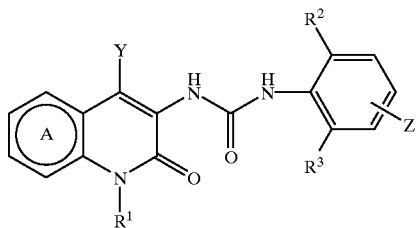

(51)

wherein Ring A, Y, $R^1$, $R^2$, $R^3$ and Z are as defined in the above [1].

[22] A pharmaceutical composition comprising the compound as set forth in any one of the above [1] to [21, or a prodrug thereof, or a pharmaceutically acceptable salt of the same.

23] An acyl-CoA: cholesterol acyl transferase (ACAT) inhibitor, which comprises as an active ingredient the compound as set forth in any one of the above [1] to [21], or a prodrug thereof, or a pharmaceutically acceptable salt of the same.

[24] An agent for treatment of hyperlipidemia or atherosclerosis, which comprises as an active ingredient the compound as set forth in any one of the above [1] to [21], or a prodrug thereof, or a pharmaceutically acceptable salt of the same.

[25] A use of the compound as set forth in any one of the above [1] to [21], or a prodrug thereof, or a pharmaceutically acceptable salt of the same, in preparation of an acyl-CoA: cholesterol acyl transferase (ACAT) inhibitor.

[26] A use of the compound as set forth in any one of the above [1] to [21], or a prodrug thereof, or a pharmaceutically acceptable salt of the same, in preparation of an agent for treatment of hyperlipidemia or atherosclerosis.

[27] A method for inhibiting acyl-CoA: cholesterol acyl transferase (ACAT) in a patient in need, which comprises administering a therapeutically effective amount of the. compound as set forth in any one of the above [1] to [21], or a prodrug thereof, or a pharmaceutically acceptable salt of the same to said patient.

[28] A method for treating hyperlipidemia or atherosclerosis in a patient in need, which comprises administering a therapeutically effective amount of the compound as set forth in any one of the above [1] to [21], or a prodrug thereof, or a pharmaceutically acceptable salt of the same to said patient.

Each group in the present invention is explained below. Unless defined otherwise, the definition for each group should be applied to cases wherein said group is a part of another substituent.

The term "lower" in the present invention means that an alkyl moiety described with "lower" is a lower alkyl group, and the lower alkyl group includes a lower alkyl group having 1 to 6 carbon atoms such as methyl, ethyl, propyl, 2-propyl, butyl, t-butyl, pentyl, hexyl, etc.

The halogen atom is fluorine atom, chlorine atom, bromine atom, or iodine atom.

Ring A is a substituted or unsubstituted pyridine ring, and the nitrogen atom thereof may be at any position except for the fused positions of the fused ring, and the preferable Ring A is one of the groups of the following formulae (a), (b) and (c).

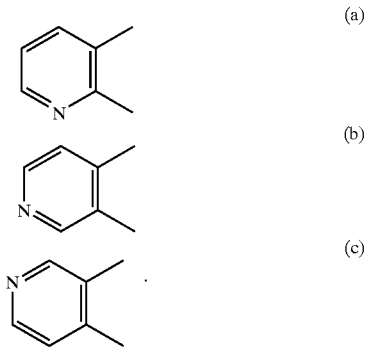

The substituent of the pyridine ring may be, for example, a lower alkyl group, a halogen atom, a cyano group, a trifluoromethyl group, a nitro group, an amino group, a mono-lower alkylamino group, a di-lower alkylamino group, a hydroxy group, a lower alkoxy group, a lower alkylthio group, a lower alkylsulfinyl group, a lower alkylsulfonyl group, etc. The substituted pyridine ring has one or more substituents which are the same or different.

The alkyl group includes, for example, a straight chain or branched chain alkyl group having 1 to 15 carbon atoms, such as methyl, ethyl, propyl, isopropyl, butyl, 2-butyl, 2-methylpropyl, 1,1-dimethylethyl, pentyl, 3-pentyl, 3-methylbutyl, hexyl, 3-hexyl, 4-methylpentyl, 4-heptyl, octyl, 4-octyl, decyl, undecyl, pentadecyl, etc.

The alkenyl group includes, for example, a straight chain or branched chain alkenyl group having 2 to 15 carbon atoms, such as vinyl, allyl, 2-propenyl, 2-methyl-2-propenyl, 2-butenyl, 3-butenyl, 3-methyl-2-butenyl, 4-pentenyl, 3-hexenyl, 3-ethyl-2-pentenyl, 4-ethyl-3-hexenyl, etc.

The alkynyl group includes, for example, a straight chain or branched chain alkynyl group having 3 to 15 carbon atoms, such as 2-propynyl, 3-butynyl, 4-pentynyl, 3-hexynyl, 5-methyl-2-hexynyl, 6-methyl-4-heptynyl, etc.

The cycloalkyl group includes, for example, a cycloalkyl group having 3 to 8 carbon atoms, such as cyclopropyl, cyclobutyl, cyclopentyl, cyclohexyl, cycloheptyl, cyclooctyl, etc.

The aromatic group for Y includes, for example, an aryl group and a heteroaryl group.

The aryl group includes, for example, an aryl group having carbon atoms of not more than 10, such as phenyl group, naphthyl group, etc.

The heteroaryl group includes, for example, a 5- to 6-membered monocyclic group having 1 to 2 nitrogen atoms, a 5- to 6-membered monocyclic group having 1 to 2 nitrogen atoms and one oxygen atom or one sulfur atom, a 5-membered monocyclic group having one oxygen atom or one sulfur atom, a bicyclic group formed by fusing a 6-membered ring and a 5- or 6-membered ring and having 1 to 4 nitrogen atoms, such as 2-pyridyl, 3-pyridyl, 4-pyridyl, 2-imidazolyl, pyrazinyl, 2-pyrimidinyl, 3-pyridazinyl, 3-oxodiazolyl, 2-thiazolyl, 3-isothiazolyl, 2-oxazolyl, 3-isoxazolyl, 2-furyl, 3-furyl, 2-thienyl, 3-thienyl, 2-quinolyl, 8-quinolyl, 2-quinazolinyl, 8-purinyl, etc.

The substituted aromatic group has one or more substituents which are the same or different, and the substituents are, for example, a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkyl-aminocarbonyl group, a carboxyl group, a lower alkoxycarbonyl group, a lower alkylthio group, a lower alkylsulfinyl group, a lower alkylsulfonyl group, a lower alkanoylamino group, a lower alkylsulfonamido group, or a group of the formula: —$M^1$—$E^1$—T {$M^1$ is a direct bond, an oxygen atom, a sulfur atom, or a group of the formula: —$NR^{61}$— ($R^{61}$ is a hydrogen atom or a lower alkyl group), $E^1$ is a divalent hydrocarbon group having 1 to 8 carbon atoms and optionally containing an unsaturated bond, T is a hydroxy group, a halogen atom, a carboxyl group, a lower alkoxycarbonyl group, a benzyloxycarbonyl group, a cyano group, a benzyloxy group, a lower alkoxy group, a lower alkanoyloxy group, a lower alkylthio group, a lower alkylsulfinyl group, a lower alkylsulfonyl group, a methanesulfonyloxy group, an alkyl-substituted or unsubstituted benzenesulfonyloxy group, a lower alkanoylamino group, a lower alkoxycarbonylamino group, a lower alkylsulfonamido group, a phthalimido group, a substituted or unsubstituted heteroaryl group, or a group of the formula: —$NR^{41}R^{51}$ ($R^{41}$ and $R^{51}$ are independently a hydrogen atom, a lower alkoxy-substituted or unsubstituted lower alkyl group, a cycloalkyl group, a lower alkoxycarbonyl group, or an aralkyl group, or $R^{41}$ and $R^{51}$ may combine each other, and with the adjacent nitrogen atom to which they bond, form a saturated cyclic amino group having 4 to 8 carbon atoms as ones forming the said ring, and optionally having one —$NR^{81}$— ($R^{81}$ is a hydrogen atom, a substituted or unsubstituted lower alkyl group, a substituted or unsubstituted phenyl group, a substituted or unsubstituted benzyl group, or a lower alkoxycarbonyl group) or one oxygen atom in the cycle thereof), or a group of the formula: —C(=O)$NR^{41}R^{51}$ ($R^{41}$ and $R^{51}$ are as defined above)}.

The substituted lower alkyl group, the substituted phenyl group and the substituted benzyl group for $R^8$ or $R^{81}$ have one or more substituents which are the same or different, and the substituents are, for example, a hydroxy group, a halogen atom, or a lower alkoxy group.

The divalent hydrocarbon group having 1 to 8 carbon atoms and optionally containing an unsaturated bond includes, for example, an alkylene chain such as methylene, ethylene, trimethylene, tetramethylene, pentamethylene, hexamethylene, etc., an alkenylene chain such as propenylene, butenylene, etc., or an alkynylene chain such as ethynylene, propynylene, butynylene, etc.

The heteroaryl group for Q, W or T includes, for example, a 5- to 6-membered cyclic group having 1 to 3 nitrogen atoms, a 5-membered cyclic group having one oxygen atom or one sulfur atom, or a bicyclic group formed by fusing a 6-membered ring and a 5- or 6-membered ring, and having 1 to 4 nitrogen atoms, such as 1-pyrrolyl, 1-pyrazolyl, 1-imidazolyl, 1,2,4-triazol-1-yl, 2-pyridyl, 3-pyridyl, 4-pyridyl, 2-thienyl, 3-thienyl, 2-furyl, 3-furyl, 2-quinolyl, etc. The substituted heteroaryl group for Q, W or T has one or more substituents which are the same or different, and the substituents are, for example, a lower alkyl group, a lower alkoxy group, or a halogen atom.

The cyclic amino group formed by —$NR^4R^5$ or —$NR^{41}R^{51}$ includes, for example, a group having 6 atoms as ones forming a ring, i.e., a 6-membered cyclic group such as 1-piperidinyl, 4-morpholinyl, 4-lower alkyl-1-piperazinyl, 4-phenyl-1-piperazinyl, or 4-benzyl-1-piperazinyl, etc., a 5-membered cyclic group such as 1-pyrrolidinyl, or a 7-membered cyclic group such as 1-homopiperidinyl, etc.

The substituted alkyl group, the substituted cycloalkyl group, the substituted alkenyl group, and the substituted alkynyl group have one or more substituents which are the same or different, and the substituents are, for example, a halogen atom, a cyano group, a phenoxy group, a benzyloxy group, a trifluoromethyl group, a hydroxy group, a lower alkoxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a lower alkoxycarbonylamino group, a carboxyl group, a lower alkoxycarbonyl group, a lower alkylthio group, a lower alkylsulfinyl group, a lower alkylsulfonyl group, a lower alkanoylamino group, a lower alkylsulfonamido. group, a phthalimido group, a heteroaryl group, or a group of the formula: —$NR^{41}R^{51}$ ($R^{41}$ and $R^{51}$ are as defined above).

The substituted alkyl group includes an alkyl group having 1 to 6 carbon atoms which is substituted by a substituted or unsubstituted cycloalkyl group, or an aralkyl group or a substituted aralkyl group.

The aralkyl group includes an alkyl group having 1 to 6 carbon atoms which is substituted by the above-mentioned aryl group, for example, benzyl, 1-phenylethyl, 2-phenylethyl, 2-naphthylmethyl, etc.

The preferable groups for Y are, for example, a substituted or unsubstituted phenyl group, or a substituted or unsubstituted pyridyl group. The substituted phenyl group and the substituted pyridyl group have one or more substituents which are the same or different, and the preferable substituents are, for example, a halogen atom such as fluorine atom, chlorine atom, etc., a cyano group, a trifluoromethyl group, a nitro group, a hydroxy group, a methylenedioxy group, a lower alkyl group, a lower alkoxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, a lower alkylsulfonamido group, or a group of the formula: —$M^1$—$E^1$—T ($M^1$, $E^1$ and T are as defined above).

The preferable groups for $M^1$ are, for example, a direct bond or an oxygen atom.

The preferable groups for E are, for example, a straight alkylene, alkenylene or alkynylene chain having 1 to 6 carbon atoms, and the more preferable ones are a straight alkylene or alkynylene chain having 1 to 3 carbon atoms.

The preferable groups for T are, for example, a hydroxy group, a cyano group, a lower alkoxy group, a lower alkanoyloxy group, a lower alkanoylamino group, a heteroaryl group, or a group of the formula: —$NR^{41}R^{51}$ ($R^{41}$ and $R^{51}$ are as defined above), and the more preferable one is a heteroaryl group such as 2-pyridyl, 3-pyridyl, 4-pyridyl, 2-methyl-3-pyridyl, 1-imidazolyl, 1,2,4-triazol-1-yl, etc., or a group of the formula: —$NR^{41}R^{51}$.

The preferable group of the formula: —$NR^{41}R^{51}$ includes, for example, dimethylamino, diethylamino, diisopropylamino, 1-pyrrolidinyl, 1-piperidinyl, morpholino, 4-methylpiperidinyl, etc.

The more preferable groups for Y are, for example, a phenyl group being substituted by a lower alkyl group or a lower alkoxy group, or a pyridyl group being substituted by a lower alkyl group or a lower alkoxy group.

The preferable groups for $R^1$ are, for example, a hydrogen atom, a substituted or unsubstituted alkyl group, or a substituted or unsubstituted alkenyl group. The substituted alkyl group and the substituted alkenyl group have one or more substituents which are the same or different, and the preferable substituents are, for example, a halogen atom such as fluorine atom or chlorine atom, a cyano group, a benzyloxy group, a hydroxy group, a lower alkoxy group, a lower alkanoyloxy group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, an aryl group, a lower alkanoylamino group, a lower alkylsulfonamido group, a phthalimido group, or a heteroaryl group. The more preferable substituents are, for example, a fluorine atom, a chlorine atom, a cyano group, a hydroxy group, a lower alkoxy group, a carbamoyl group, a 2-pyridyl group, a 3-pyridyl group, a 4-pyridyl group, etc. The further more preferable substituents for $R^1$ are, for example, an unsubstituted alkyl or alkenyl group.

The preferable groups for $R^2$ are, for example, a hydrogen atom, a methyl group, an ethyl group, a propyl. group, or an isopropyl group. The preferable groups for $R^3$ are, for example, an isopropyl group or a tert-butyl group.

The preferable groups for $D^1$ are, for example, a methylene group or an ethylene group. The preferable groups for Q are, for example, a hydroxy group, a substituted or unsubstituted heteroaryl group, or a group of the formula: —$NR^4R^5$ ($N^4$ and $R^5$ are as defined above). The more preferable groups are, for example, a hydroxy group, a 1-pyrazolyl group, a 3,5-dimethyl-1-pyrazolyl group, a 1-imidazolyl group, a 2-methyl-1-imidazolyl group, a 1,2,4-triazol-1-yl group, a 1-piperidinyl group, a 1-pyrrolidinyl group, a 4-methyl-1-piperazinyl group, a morpholino group, a diethylamino group or a dipropylamino group.

The preferable groups for $D^2$ are, for example, a direct bond, a methylene group or an ethylene group. The preferable groups for M are, for example, an oxygen atom, or a group of the formula: —NHC(=O)—, —C(=O)NH—, or —$NR^6$—.

The preferabley groups for E are, for example, methylene, ethylene or trimethylene.

The preferable groups for W are, for example, a hydroxy group, a substituted or unsubstituted heteroaryl group, or a group of the formula: —$NR^4R^5$. The more preferable groups are, for example, a hydroxy group, a 2-pyridyl group, a 3-pyridyl group, a 4-pyridyl group, a 1-pyrazolyl group, a 3,5-dimethyl-1-pyrazoyl group, a 1-imidazolyl group, a 2-methyl-1-imidazolyl group, a 1,2,4-triazol-1-yl group, a 1-piperidinyl group, a 1-pyrrolidinyl group, a 4-methyl-1-piperazinyl group, a morpholino group, a diethylamino group, or a dipropylamino group.

The preferable groups represented by the following formula (2):

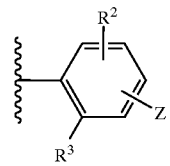

(2)

are, for example 2,6-diisopropyl-4-(2-pyridylmethoxy) phenyl group, 2,6-diisopropyl-4-(3-pyridylmethoxy)phenyl group, 2,6-diisopropyl-4-(4-pyridylmethoxy)phenyl group, 2,6-diisopropyl-4-{2-(1-piperidinyl)ethoxy}phenyl group, 2,6-diisopropyl-4-{3-(1-piperidinyl)propoxy}phenyl group, 2,6-diisopropyl-4-{2-(1-pyrrolidinyl)ethoxy}phenyl group, 2,6-diisopropyl-4-{2-(morpholino)ethoxy}phenyl group, 2,6-diisopropyl-4-{2-(4-methyl-1-piperazinyl) ethoxy}phenyl group, 2,6-diisopropyl-4-{2-(1,2,4-triazol-1-yl)ethoxy}phenyl group, 2,6-diisopropyl-4-{3-(1,2,4 triazol-1-yl)propoxy}phenyl group, 2-tert-butyl-5-hydroxymethylphenyl group, 2-tert-butyl-5-(1-pyrazolyl) methylphenyl group, 2-tert-butyl-5-{2-(1-pyrazolyl) ethyl}phenyl group, 2-tert-butyl-5-(3,5-dimethyl-1-pyrazolyl)methylphenyl group, 2-tert-butyl-5-(1-imidazolyl)methylphenyl group, 2-tert-butyl-5-{2-(1-imidazolyl)ethyl}phenyl group, 2-tert-butyl-5-(2-methyl-1-imidazolyl)methylphenyl group, 2-tert-butyl-5-(1,2,4-triazol-1-yl)methylphenyl group, 2-tert-butyl-5-{2-(1,2,4-triazol-1-yl)ethyl}phenyl group, 2-tert-butyl-5-(1-piperidinyl)methylphenyl group, 2-tert-butyl-5-(1-pyrrolidinyl)methylphenyl group, 2-tert-butyl-5-(4-methyl-1-piperazinyl)methylphenyl group, 2-tert-butyl-5-morpholinomethylphenyl group, 2-tert-butyl-5-diethylaminomethylphenyl group, 2-tert-butyl-5-dipropylaminomethylphenyl group, 2-tert-butyl-5-(2-pyridyl)methylaminomethylphenyl group, 2-tert-butyl-5-(3-pyridyl)methylaminomethyl group, 2-tert-butyl-5-(4-pyridyl)methylaminomethylphenyl group, 2-tert-butyl-5-{N-(2-pyridyl)methyl-N-methyl}aminomethylphenyl group, 2-tert-butyl-5-{N-(3-pyridyl)methyl-N-methyl}aminomethylphenyl group, or 2-tert-butyl-5-{N-(4-pyridyl)methyl-N-methyl}aminomethylphenyl group.

The "prodrug" includes a compound which can easily be hydrolyzed in the living body, and can reproduce the compound of the formula (1) or (51). The "prodrug" is, for example, when such a compound of the formula (1) or (51) has a carboxyl group, then ones wherein said carboxyl group is replaced by an alkoxycarbonyl group, an alkylthiocarbonyl group, or an alkylaminocarbonyl group, or when a compound of the formula (1) or (51) has an amino group, then ones wherein said amino group is substituted by an alkanoyl group to form an alkanoylamino group, or substituted by an alkoxycarbonyl group to form an alkoxycarbonylamino group, or converted to an acyloxymethylamino group or a hydroxyamine. When a compound of the formula (1) or (51) has a hydroxy group, the prodrug thereof is, for example, compounds wherein said hydroxy group is substituted by an acyl group as mentioned above and converted to an acyloxy group, or converted to a phosphate ester, or converted to an acyloxymethyloxy group. The alkyl moiety of groups being used for making a prodrug may be the above-mentioned alkyl groups, and said alkyl group may optionally be substituted, for example, by an alkoxy group having 1 to 6 carbon atoms, etc. The preferable example are, for example, in the compounds wherein a carboxyl group is converted to an alkoxycarbonyl group, a lower (e.g., having 1 to 6 carbon atoms) alkoxycarbonyl group such as methoxycarbonyl, ethoxycarbonyl, or a lower (e.g., having 1 to 6 carbon atoms) alkoxycarbonyl group being substituted by an alkoxy group such as methoxymethoxycarbonyl, ethoxymethoxycarbonyl, 2-methoxyethoxycarbonyl, 2-methoxyethoxymethoxycarbonyl, or pivaloyloxymethoxycarbonyl.

The acid for forming an acid addition salt includes, for example, inorganic acids such as hydrochloric acid, hydrobromic acid, hydroiodic acid, sulfuric acid, nitric acid, etc., or organic acids such as acetic acid, oxalic acid, citric acid, malic acid, tartaric acid, fumaric acid, maleic acid, methanesulfonic acid, benzenesulfonic acid, etc.

When the present compounds have a carboxyl group, etc., then the present compounds may be in the form of a salt with an organic base such as diethanolamine salt, ethylenediamine salt, or N-methylglucamine salt, or a salt with an alkaline earth metal such as calcium salt or magnesium salt, or a salt with an alkali metal such as lithium salt, potassium salt, or sodium salt.

The present compounds may have a stereoisomer due to an asymmetric carbon atom thereof. In such cases, the present compounds also include each isomer or a mixture thereof.

The present compounds may be in the form of an anhydrous product thereof, or in the form of a solvate thereof such as hydrate.

The present compounds can be administered either parenterally or orally when used as the above-mentioned drug. The present compounds can be formulated into liquid preparations such as solutions, emulsions, suspensions, etc., and can be administered in the form of an injection, and if necessary, buffering agents, solubilizers and isotonic agents may be added thereto. The present compounds can also be administered rectally in the form of a suppository. The present compounds can also be administered orally in the form of a conventional administration form such as tablets, capsules, syrups, and suspension. These pharmaceutical preparations may be formulated by mixing an active ingredient with conventional carriers or diluents, binding agents or stabilizers by a conventional manner.

The dosage and the frequency of administration of the present compounds may vary according to the conditions, ages, weights of the patients and the administration form, etc., but the present compounds can usually be administered orally in a dose of 1 to 500 mg per day in adult, once a day, or divided into 2–4 dosage units.

The naphthyridine derivative of the active ingredient of the present invention may be prepared by the following processes.

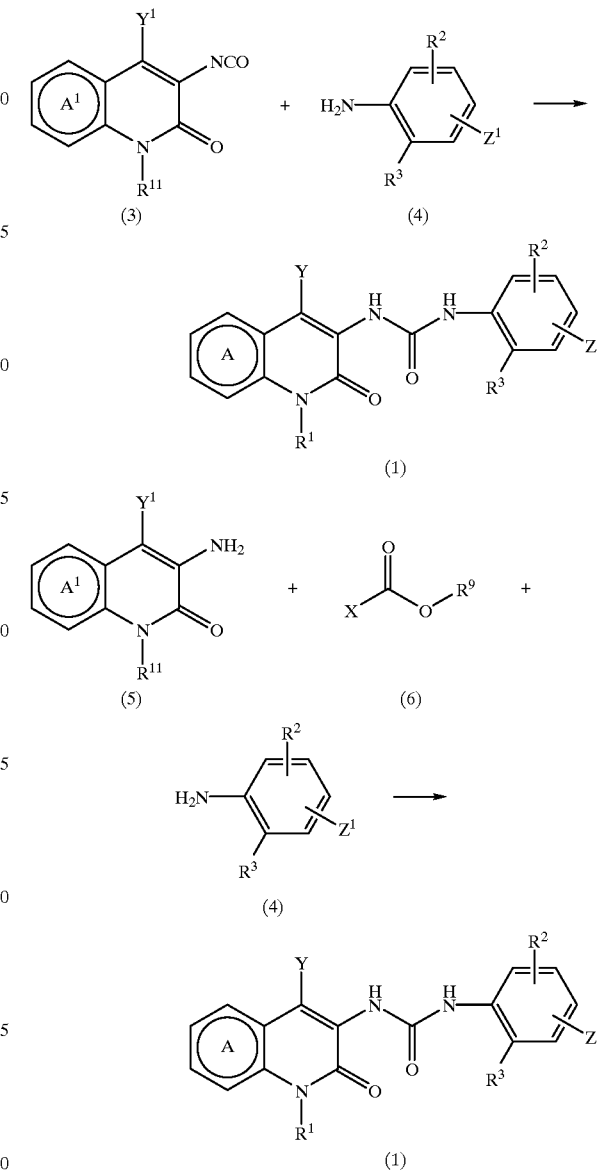

wherein Ring A, Y. $R^1$, $R^2$, $R^3$ and Z are as defined above; Ring $A^1$ is the same groups for Ring A, but when these groups contain a reactive group as a substituent such as an amino group, an alkylamino group, a hydroxy group, etc., then these reactive groups should be protected; $R^{11}$ is the same groups for $R^1$, but when these groups contain a reactive group as a substituent such as an amino group, an alkylamino group, a hydroxy group, a carboxyl group, etc., then these reactive groups should be protected; $Y^1$ is the same groups for Y, but when these groups contain a reactive group as a substituent such as an amino group, an alkylamino group, a hydroxy group, a carboxyl group, etc., then these reactive groups should be protected; $Z^1$ is the same groups for Z, but when these groups contain a reactive group as a substituent such as an amino group, an alkylamino group, a hydroxy group, a carboxyl group, etc., then these reactive groups should be protected; $R^9$ is a lower alkyl group or a phenyl group, and X is a hydrogen atom such as a chlorine atom or a bromine atom.

The isocyanate derivative (3) and the amine derivative (4) or an acid addition salt thereof are usually reacted in a solvent at a temperature of from 0° C. to 120° C., preferably at a temperature of from room temperature to a boiling point of the solvent to be used, and if necessary, the protecting groups of the product are removed to give the urea derivative (1). The solvent may be any solvent which does not disturb the reaction, and preferably be ethers (e.g., ethyl ether, dimethoxyethane, isopropyl ether, tetrahydrofuran, dioxane, etc), aromatic hydrocarbons (e.g., benzene, toluene, xylene, etc.), esters (e.g., methyl acetate, ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitrites (e.g., acetonitrile, isobutyronitirile, etc.), N,N-dimethylformamide, dimethylsulfoxide, and the like.

When the amine derivative (4) is used in the form of an acid addition salt thereof, the reaction may smoothly proceed by converting the compound (4) into a free form, if necessary. In this case, an agent for converting the compound (4) into a:free form is preferably a tertiary amine such as triethylamine, etc., or pyridine.

Alternatively, the urea compound (1) can also be obtained by reacting the amine derivative (5) and the halocarbonate (6) at a temperature of from 0° C. to 80° C. to give a carbamate, which is further reacted with the amine derivative (4) at a temperature of from room temperature to a boiling point of the solvent to be used, or a temperature of from room temperature to 100° C., and further if necessary, followed by removing protecting groups from the product.

The halocarbonate (6) includes, for example, methyl chlorocarbonate, ethyl chlorocarbonate, isobutyl chlorocarbonate, phenyl chlorocarbonate, etc. The reaction is usually carried out in a solvent, and the solvent may be any solvent which does not disturb the reaction, for example, ethers (e.g., ethyl ether, isopropyl ether, tetrahydrofuran, dioxane, etc.), aromatic hydrocarbons (e.g., benzene, toluene, xylene, etc.), esters (e.g., methyl acetate, ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitrites (e.g., acetonitrile, isobutyronitirile, etc.), N,N-dimethylformamide, dimethylsulfoxide, etc.

In addition, in a similar manner, the urea compound (1) can also be obtained by reacting first the amine derivative (4) and the halocarbontae (6), followed by reacting the resultant with the amine derivative (5).

The protecting groups for amino group, alkylamino group, hydroxy group, carboxyl group, etc., may be conventional protecting groups which are used in the field of the organic chemistry, for example, the protecting group for hydroxy group may be tetrahydropyranyl group, acetyl group, etc., and the protecting group for amino group may be benzyl group, etc., and these protecting groups may be introduced and removed by a conventional method, such as by a method disclosed in PROTECTIVE GROUPS IN ORGANIC SYNTHESIS, 2nd ed., John Wiley & Sons, Inc.; New York.

Among the urea derivatives (1), the derivative of the following formula (7) may be converted into other urea derivative of the formula (9) by reacting with an alkylating agent of the formula (8), and if necessary, followed by removing the protecting groups of the product.

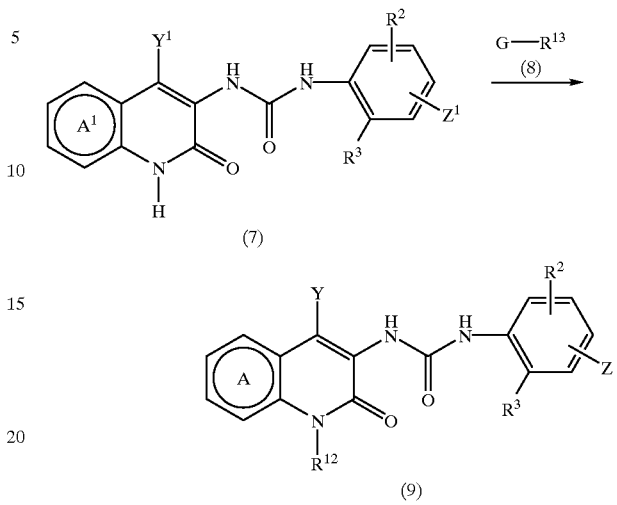

wherein Ring A, Ring $A^1$, $R^2$, $R^3$, Y, $Y^1$, Z and $Z^1$ are as defined above, $R^{12}$ is the same groups for $R^1$ except for a hydrogen atom, $R^{13}$ is the same groups for $R^{12}$ but when these groups contain a reactive group as a substituent such as an amino group, an alkylamino group, a hydroxy group, a carboxyl group, etc., then these reactive groups should be protected, and G is a leaving group.

The alkylation reaction is carried out in a solvent at a temperature of from 0° C. to 100° C., preferably at a temperature of from room temperature to 70° C. in the presence of a base. The solvent may be any solvent which does not disturb the reaction, for example, ethers (e.g., diethyl ether, dimethoxyethane, tetrahydrofuran, dioxane, etc.), aromatic hydrocarbons (e.g., benzene, toluene, xylene, etc.), ketones (e.g., acetone, methyl ethyl ketone, etc.), nitriles (e.g., acetonitrile, isobutyronitirile, etc.), and amides (e.g., N,N-dimethylformamide, N,N-dimethylacetamide, etc.). The base includes, for example, sodium hydride, potassium carbonate, sodium carbonate, triethylamine, diisopropylethylamine, pyridine, etc. The leaving group represented by G is usually a halogen atom such as chlorine atom, bromine atom, iodine atom, etc., a lower alkylsulfonyloxy group such as methanesulfonyloxy group, or an aromatic sulfdnyloxy group such as p-toluenesulfonyloxy group.

The substituents of Ring A, Z, Y or $R^1$ in the urea derivative (1) thus obtained can be converted into others, if necessary. For example, a lower alkylthio group can be converted into a lower alkylsulfonyl group by oxidization. A nitro group is converted into an amino group by reduction. An amino group can be alkylated to a mono- or di-alkylamino group, or an amino group can also be acylated. A 3-chloropropoxy group is converted into a 3-(1-imidazolyl)propoxy group. Moreover, when Z is an amino group, said amino group can be converted into a hydroxy group. Such conversion reactions can be carried out by using a well-known technique which is usually applied in the organic chemistry field. As one of the conversion reactions of the substituents, the reactions of the following formulae can be carried out.

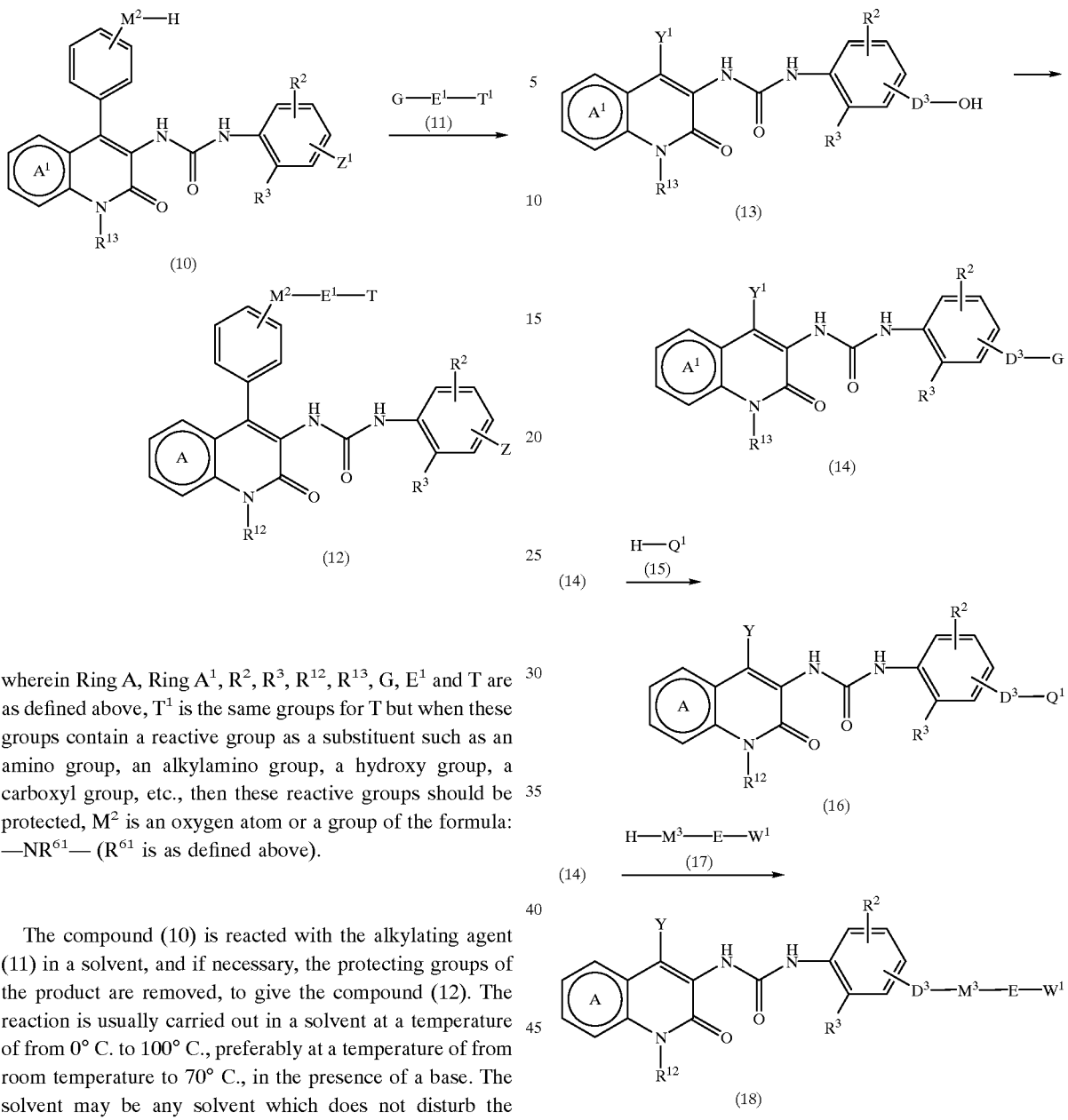

wherein Ring A, Ring $A^1$, $R^2$, $R^3$, $R^{12}$, $R^{13}$, G, $E^1$ and T are as defined above, $T^1$ is the same groups for T but when these groups contain a reactive group as a substituent such as an amino group, an alkylamino group, a hydroxy group, a carboxyl group, etc., then these reactive groups should be protected, $M^2$ is an oxygen atom or a group of the formula: $-NR^{61}-$ ($R^{61}$ is as defined above).

The compound (10) is reacted with the alkylating agent (11) in a solvent, and if necessary, the protecting groups of the product are removed, to give the compound (12). The reaction is usually carried out in a solvent at a temperature of from 0° C. to 100° C., preferably at a temperature of from room temperature to 70° C., in the presence of a base. The solvent may be any solvent which does not disturb the reaction, for example, ethers (e.g., diethyl ether, dimethoxethane, tetrahydrofuran, dioxane, etc.), aromatic hydrocarbons (e.g., benzene, toluene, xylene, etc.), ketones (e.g., acetone, methyl ethyl ketone, etc.), nitrites (e.g., acetonitrile, isobutyronitrile, etc.), and amides (e.g., N,N-dimethylformamide, N,N-dimethylacetamide, etc.). The base may be, for example, sodium hydride, potassium carbonate, sodium carbonate, triethylamine, diisopropylethylamine, pyridine, etc. When potassium carbonate or sodium carbonate is used, the yield of the reaction may optionally be increased by addition of sodium iodide or potassium iodide. The leaving group represented by G is usually halogen atoms such as chlorine atom, bromine atom, iodine atom, etc., a lower alkylsulfonyloxy group such as methanesulfonyloxy group, or an aromatic sulfonyloxy group such as p-toluenesulfonyloxy group, etc.

wherein Ring A, Ring $A^1$, $R^2$, $R^3$, $R^{12}$, $R^{13}$, Y, $Y^1$, G and E are as defined above, $M^3$ is an oxygen atom or a sulfur atom, or a group of the formula: $-NR^6-$ ($R^6$ is as defined above), $W^1$ is the same groups for W but when these groups contain a reactive group as a substituent such as an amino group, an alkylamino group, a hydroxy group, etc., then these reactive groups should be protected, $Q^1$ is a group of the formula: $-NR^4R^5$ ($R^4$ and $R^5$ are as defined above), or a heteroaryl group, provided that said heteroaryl group should be one wherein the nitrogen atom thereof is attached to $D^3$, and $D^3$ is a divalent hydrocarbon group having 1 to 8 carbon atoms, and optionally containing an unsaturated bond.

The compound of the formula (16) is obtained by converting the alcohol moiety of the alcohol derivative (13) into a leaving group, reacting the resultant with the compound of the formula: $H-Q^1$, if necessary, followed by removing the protecting groups.

When the leaving group is a halogen atom (e.g., chlorine, bromine, iodine), the conversion into a leaving group may be carried out by reacting with a halogenating agent such as thionyl halides (e.g., thionyl chloride, etc.), phosphorous trihalides (e.g., phosphorus tribromide, etc.), a mixture of triphenylphosphine-carbon tetrahalide such as triphenylphosphine-carbon tetrachloride, triphenylphosphine-carbon tetrabromide, triphenylphosphine-carbon tetraiodide, in a solvent at a temperature of from −10° C. to 100° C., preferably at a temperatuer of from 10° C. to 50° C. The solvent may be any solvent which does not disturb the reaction, for example, ethers (e.g., tetrahydrofuran, dioxane, etc.), aromatic hydrocarbons (e.g., benzene, toluene, etc.), halogenated hydrocarbons (e.g., dichloromethane, chloroform, carbon tetrachloride, 1,2-dichloroethane, etc.), and the halogenated hydrocarbon is preferably used. When the leaving group is a lower alkyl- or aromatic sulfonyloxy group, the conversion into such a leaving group may usually be carried out by reacting with a lower alkyl or arylsulfonyl chloride in a solvent at a temperature of from −20° C. to 80° C., preferably at a temperature of from 0 to 30° C. in the presence of a base. The solvent may be any solvent which does not disturb the reaction, for example, ethers (e.g., tetrahydrofuran, dioxane, etc.), aromatic hydrocarbons (e.g., benzene, toluene, etc.), or halogenated hydrocarbons (e.g., dichloromethane, chloroform, carbon tetrachloride, 1,2-dichloroethane. etc.). The base includes, for example, triethylamine, diisopropylethylamine, pyridine, etc.

The introduction of $Q^1$ is usually carried out by reacting with a compound of the formula: $H-Q^1$ in a solvent at a temperature of from 0° C. to 150° C., preferably at a temperature of from room temperature to 120° C. In general, the reaction can preferably proceed by using an excess amount of the compound of the formula: $H-Q^1$, or using a base. The base includes, for example, potassium carbonate, sodium carbonate, triethylamine, diisopropylethylamine, pyridine, etc. When potassium carbonate or sodium carbonate is used, the efficiency of the reaction may optionally be increased by addition of sodium iodide or potassium iodide.

The compound of the formula (14); can be converted into the compound of the formula (18) by reacting with the compound (17) in a solvent, and if necessary, followed by removing the protecting groups. The reaction is usually carried out in a solvent at a temperature of from 0° C. to 100° C., preferably at a temperature of from room temperature to 70° C. in the presence of a base. The solvent may be any solvent which does not disturb the reaction, for example, ethers (e.g., tetrahydrofuran, dioxane, etc.), aromatic hydrocarbons (e.g., benzene, toluene, etc.), ketones (e.g., acetone, 2-butanone, etc.), or dimethylformamide, etc. The base may be an alkali metal carbonate such as potassium carbonate, sodium carbonate, etc., or an organic base such as triethylamine, diisopropylethylamine, pyridine, etc. When potassium carbonate or sodium carbonate is used, the yield of the reaction may optionally be increased by addition of sodium iodide or potassium iodide.

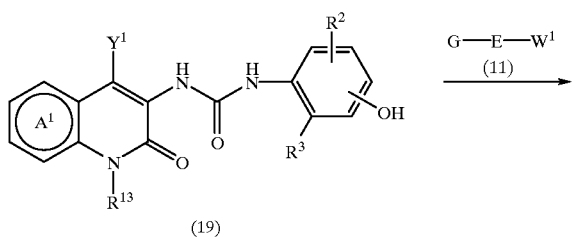

(19)

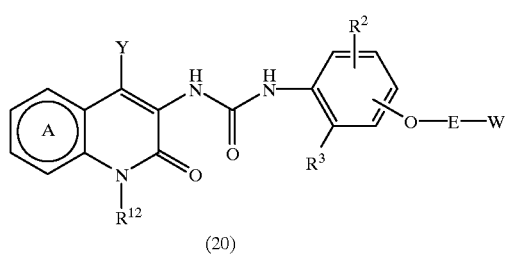

(20)

wherein Ring A, Ring $A^1$, $R^2$, $R^3$, $R^{12}$, $R^{13}$, Y, $Y^1$, G, E, W and $W^1$ are as defined above.

The compound of the formula (20) is obtained by reacting the compound (19) with the alkylating agent of the formula (11) in a solvent, if necessary, followed by removing the protecting groups. The reaction is usually carried out in a solvent at a temperature of from 0° C. to 100° C., preferably at a temperature of from room temperature to 70° C. in the presence of a base. The solvent may be any solvent which does not disturb the reaction, for example, ethers (e.g., tetrahydrofuran, dioxane, etc.), aromatic hydrocarbons (e.g., benzene, toluene, etc.), ketones (e.g., acetone, 2-butanone, etc.), dimethylformamide, etc. The base may be, for example, sodium hydride, potassium carbonate, sodium carbonate, triethylamine, djisopropylethylamine, pyridine, etc. When potassium carbonate or sodium carbonate is used, the yield of the reaction may optionally be increased by addition of sodium iodide or potassium iodide. The leaving group represented by G is usually a halogen atom such as chlorine atom, bromine atom, iodine atom, etc., a lower alkylsulfonyloxy group such as methanesulfonyloxy group, or an aromatic sulfonyloxy group such as p-toluenesulfonyloxy group.

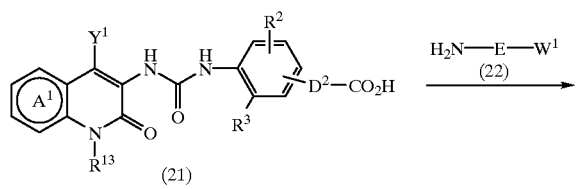

(21)

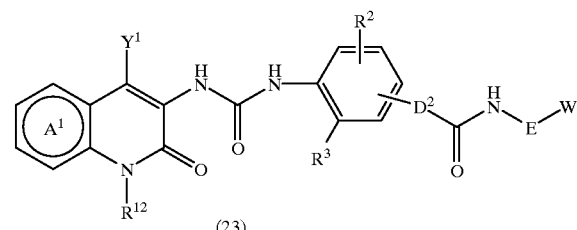

(23)

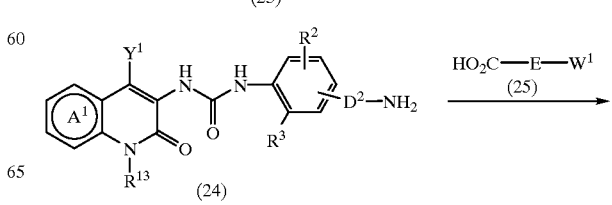

(24)

-continued

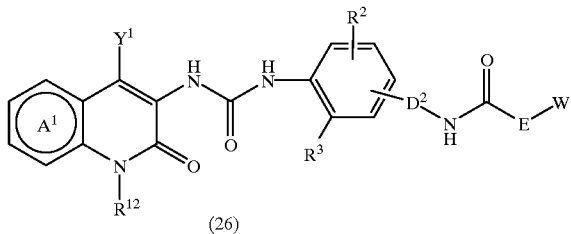

(26)

wherein Ring A, Ring $A^1$, $R^2$, $R^3$, $R^{12}$, $R^{13}$, Y, $Y^1$, $D^2$, E, W and $W^1$ are as defined above.

The carboxyic acid derivative of the formula (21) is condensed with the amine derivative of the formula (22) or an acid addition salt thereof using a condensing agent in a solvent at a temperature of from 0° C. to 100° C., preferably at a temperature of from 0° C. to 60° C., and if necessary, the resultant is further subjected to deprotection reaction to give the amide derivative (23). The condensing agent may be dicyclohexylcarbodiimide (DCC), 1,1'-carbonyldiimidazole, diethyl cyanophosphate (DEPC), 1-ethyl-3-(3'-dimethylaminopropyl)-carbodiimide hydrochloride (WSC), etc. The reaction may preferably proceed by addition of a base in an amount of 1 to 5 mole equivalents, preferably in an amount of 1 to 3 mole equivalents, to the amount of the amine derivative (22) or an acid addition salt thereof. The base may be a tertiary amine such as triethylamine, diisopropylethylamine, or pyridine, etc. The solvent may be any solvent which does not disturb the reaction, for example, ethers (e.g., diethyl ether, dimethoxyethane, tetrahydrofuran, dioxane, etc.), aromatic hydrocarbons (e.g., benzene, toluene, xylene, etc.), esters (e.g., ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitrites (e.g., acetonitrile, isobutyronitrile, etc.), and amides (e.g., N,N-dimethylformamide, N,N-dimethylacetamide, etc.).

Alternatively, the carboxylic acid derivative (21) is converted into a reactive derivative thereof, which is further reacted with the amine derivative (22) in a solvent at a temperature of from −10° C. to 120° C., preferably at a temperature of from 0° C. to 60° C. to give the amide derivative (23). The reactive derivative of the carboxylic acid derivative (21) may be, for example, an acid chloride, an acid bromide, an acid anhydride, or a mixed acid anhydride with methyl carbonate, ethyl carbonate, etc., and the reaction may preferably proceed by addition of a base in an amount of 1 to 5 mole equivalents, preferably in an amount of 1 to 3 mole equivalents. The base may be a tertiary amine (e.g., triethylamine, etc.), pyridine, an alkali metal carbonate (e.g., sodium carbonate, potassium carbonate, etc.), and an alkali metal hydrogen carbonate (e.g., sodium hydrogen carbonate, etc.). The solvent may be any solvent which does not disturb the reaction, for example, ethers (e.g., diethyl ether, dimethoxyethane, tetrahydrofuran, dioxane, etc.), aromatic hydrocarbons (e.g., benzene, toluene, xylene, etc.), esters (e.g., ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitrites (e.g., acetonitrile, isobutyronitrile, etc.), and amides (e.g., N,N-dimethylformamide, N,N-dimethylacetamide, etc.).

Similarly, the amide derivative of the formula (26) can be obtained from the amine derivative (24) and the carboxylic acid derivative (25).

The starting compound (3) or (5) for preparing the present compound (1) or a salt thereof may be prepared by the method disclosed in the literature (e.g., JP-A-9-48780) or a modified method thereof. The starting compound (4) is commercially available, or may be prepared by the method disclosed in the literature (e.g., JP-A-6-145125, JP-A-9-202775) or a modified method thereof. In addition, some of the compounds can be prepared by the following process.

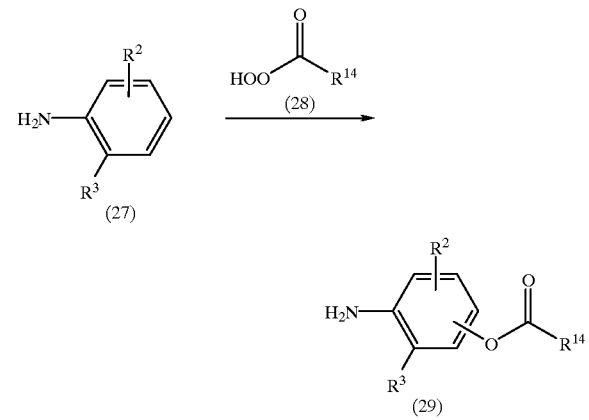

wherein $R^2$ and $R^3$ are as defined above, $R^{14}$ is an alkyl group, or a phenyl group being substituted by a lower alkyl group or a halogen atom.

The aniline derivative of the formula (21) is reacted with the peracid of the formula (22) in a solvent at a temperature of from −20° C. to 50° C., preferably at a temperature of from 0° C. to room temperature to give the aniline derivative of the formula (23). The solvent may be any solvent which does not disturb the reaction, for example, aromatic hydrocarbons (e.g., benzene, toluene, etc.), or halogenated hydrocarbons (e.g., dichloromethane, chloroform, carbon tatrachloride, 1,2-dichloroethane, etc.), and the preferable solvent is halogenated hydrocarbons. The peracid may usually be m-chloroperbenzoic acid.

The present compounds obtained by the present process, and the intermediates therefor may be purified by a conventional method, for example, column chromatography, recrystallization, etc. The solvent for recrystallization may be, for example, alcohols (e.g., methanol, ethanol, 2-propanol, etc.), ethers (e.g., diethyl ether, dimethoxyethane, tetrahydrofuran, dioxane, etc.), aromatic hydrocarbons (e.g., benzene, toluene, xylene, etc.), esters (e.g., ethyl acetate, propyl acetate, etc.), halogenated hydrocarbons (e.g., dichloromethane, chloroform, dichloroethane, chlorobenzene, dichlorobenzene, etc.), ketones (e.g., acetone, methyl ethyl ketone, etc.), nitrites (e.g., acetonitrile, isobutyronitirile, etc.), hydrocarbons (e.g., hexane, pentane, etc.), or a mixture of these solvents, which is selected according to the kinds of the compound to be recrystallized.

The present compounds obtained by the above process are exemplified as follows.

N-[1-butyl-4-(3-methoxyphenyl)-1,2-dihydro-2-oxo-1,8-naphthyridin-3-yl]-N'-[2-tert-butyl-5-(hydroxymethyl)phenyl]urea;

N-[1-butyl-4-(3-methoxyphenyl)-1,2-dihydro-2-oxo-1,8-naphthyridin-3-yl]-N'-[2-tert-butyl-5-(morpholinomethyl)phenyl]urea;

N-[1-butyl-4-(3-methoxyphenyl)-1,2-dihydro-2-oxo-1,8-naphthyridin-3-yl]-N'-[2-tert-butyl-5-(diethylaminomethyl)phenyl]urea;

N-[1-butyl-4-(3-methoxyphenyl)-1,2-dihydro-2-oxo-1,8-naphthyridin-3-yl]-N'-[2-tert-butyl-5-(dipropylamino)phenyl]urea;

N-[1-butyl-4-(3-methoxyphenyl)-1,2-dihydro-2-oxo-1,8-naphthyridin-3-yl]-N'-[2-tert-butyl-5-(piperidinomethyl)phenyl]urea;

N-[1-butyl-4-(3-methoxyphenyl)-1,2-dihydro-2-oxo-1,8-naphthyridin-3-yl]-N'-[2-tert-butyl-5-(1-pyrrolidinylmethyl)phenyl]urea;

N-[1-butyl-4-(3-methoxyphenyl)-1,2-dihydro-2-oxo-1,8-naphthyridin-3-yl]-N'-[2-tert-butyl-5-[(4-methyl-1-piperazinyl)methyl]-phenyl]urea;

N-[1-butyl-4-(3-methoxyphenyl)-1,2-dihydro-2-oxo-1,8-naphthyridin-3-yl]-N'-[2-tert-butyl-5-(1-pyrazolylmethyl)phenyl]urea;

N-[1-butyl-4-(3-methoxyphenyl)-1,2-dihydro-2-oxo-1,8-naphthyridin-3-yl]-N'-[2-tert-butyl-5-[(3,5-dimethyl-1-pyrazolyl)methyl]-phenyl]urea;

N-[1-butyl-4-(3-methoxyphenyl)-1,2-dihydro-2-oxo-1,8-naphthyridin-3-yl]-N'-[2-tert-butyl-5-(1-imidazolylmethyl)phenyl]urea;

N-[1-butyl-4-(3-methoxyphenyl)-1,2-dihydro-2-oxo-1,8-naphthyridin-3-yl]-N'-[2-tert-butyl-5-[(2-methyl-1-imidazolyl)methyl]-phenyl]urea;

N-[1-butyl-4-(3-methoxyphenyl)-1,2-dihydro-2-oxo-1,8-naphthyridin-3-yl]-N'-[2-tert-butyl-5-[(1,2,4-triazol-1-yl)methyl]-phenyl]urea;

N-[1-butyl-4-(3-methoxyphenyl)-1,2-dihydro-2-oxo-1,8-naphthyridin-3-yl]-N'-[2-tert-butyl-5-[N-(2-pyridylmethyl)aminomethyl]-phenyl]urea;

N-[1-butyl-4-(3-methoxyphenyl)-1,2-dihydro-2-oxo-1,8-naphthyridin-3-yl]-N'-[2-tert-butyl-5-[N-(3-pyridylmethyl)aminomethyl]-phenyl]urea;

N-1-butyl-4-(3-methoxyphenyl)-1,2-dihydro-2-oxo-1,8-naphthyridin-3-yl]-N'-[2-tert-butyl-5-[N-(4-pyridylmethyl)aminomethyl]-phenyl]urea;

N-[1-butyl-4-(3-methoxyphenyl)-1,2-dihydro-2-oxo-1,8-naphthyridin-3-yl]-N'-[2-tert-butyl-5-[N-(2-pyridylmethyl)-N-methyl-aminomethyl]phenyl]urea;

N-[1-butyl-4-(3-methoxyphenyl)-1,2-dihydro-2-oxo-1,8-naphthyridin-3-yl]-N'-[2-tert-butyl-5-[N-(3-pyridylmethyl)-N-methyl-aminomethyl]phenyl]urea;

N-[1-butyl-4-(3-methoxyphenyl)-1,2-dihydro-2-oxo-1,8-naphthyridin-3-yl]-N'-[2-tert-butyl-5-[N-(4-pyridylmethyl)-N-methyl-aminomethyl]phenyl]urea;

N-[1-butyl-4-(3-methoxyphenyl)-1,2-dihydro-2-oxo-1,8-naphthyridin-3-yl]-N'-[2-tert-butyl-5-(2-pyridylmethoxymethyl)-phenyl]urea;

N-[1-butyl-4-(3-methoxyphenyl)-1,2-dihydro-2-oxo-1,8-naphthyridin-3-yl]-N'-[2-tert-butyl-5-(3-pyridylmethoxymethyl)-phenyl]urea;

N-[1-butyl-4-(3-methoxyphenyl)-1,2-dihydro-2-oxo-1,8-naphthyridin-3-yl]-N'-[2-tert-butyl-5-(4-pyridylmethoxymethyl)-phenyl]urea;

N-[1-butyl-4-(3-methoxyphenyl)-1,2-dihydro-2-oxo-1,8-naphthyridin-3-yl]-N'-[2-tert-butyl-5-[3-(1,2,4-triazol-1-yl)propoxy-methylphenyl]urea;

N-[1-butyl-4-(3-methoxyphenyl)-1,2-dihydro-2-oxo-1,8-naphthyridin-3-yl]-N'-[2-isopropyl-5-(1-imidazolylmethyl)phenyl]urea;

N-[4-(3-methoxyphenyl)-1,2-dihydro-2-oxo-1,8-naphthyridin-3-yl]-N'-[2-tert-butyl-5-(1-imidazolylmethyl) phenyl]urea;

N-[1-methyl-4-(3-methoxyphenyl)-1,2-dihydro-2-oxo-1,8-naphthyridin- 3-yl]-N'-[2-tert-butyl-5-(1-imidazolylmethyl)phenyl]urea;

N-[1-ethyl-4-(3-methoxyphenyl)-1,2-dihydro-2-oxo-1,8-naphthyridin-3-yl]-N'-[2-tert-butyl-5-(1-imidazolylmethyl)phenyl]urea;

N-[1-propyl-4-(3-methoxyphenyl)-1,2-dihydro-2-oxo-1,8-naphthyridin-3-yl]-N'-[2-tert-butyl-5-(1-imidazolylmethyl)phenyl]urea;

N-[1-pentyl-4-(3-methoxyphenyl)-1,2-dihydro-2-oxo-1,8-naphthyridin-3-yl]-N'-[2-tert-butyl-5-(1-imidazolylmethyl)phenyl]urea;

N-[1-(2-methoxyethyl)-4-(3-methoxyphenyl)-1,2-dihydro-2-oxo-1,8-naphthyridin-3-yl]-N'-[2-tert-butyl-5-(1-imidazolylmethyl)phenyl]urea;

N-[1-(4-pentenyl)-4-(3-methoxyphenyl)-1,2-dihydro-2-oxo-1,8-naphthyridin-3-yl]-N'-[2-tert-butyl-5-(1-imidazolylmethyl)phenyl]urea;

N-[1-hexyl-4-(3-methoxyphenyl)-1,2-dihydro-2-oxo-1,8-naphthyridin-3-yl]-N'-[2-tert-butyl-5-(morpholinomethyl)phenyl]urea;

N-[1-(2-methoxyethyl)-4-(3-methoxyphenyl)-1,2-dihydro-2-oxo-1,8-naphthyridin-3-yl]-N'-[2-tert-butyl-5-(morpholinomethyl)phenyl]urea;

N-[1-(3-cyanopropyl)-4-(3-methoxyphenyl)-1,2-dihydro-2-oxo-1,8-naphthyridin-3-yl]-N'-[2-tert-butyl-5-(morpholinomethyl)phenyl]urea;

N-[4-(3-methoxyphenyl)-1,2-dihydro-2-oxo-1,8-naphthyridin-3-yl]-N'-[2-tert-butyl-5-(morpholinomethyl)phenyl]urea;

N-[1-butyl-4-(2-methoxyphenyl)-1,2-dihydro-2-oxo-1,8-naphthyridin-3-yl]-N'-[2-tert-butyl-5-(1-imidazolylmethyl)phenyl]urea;

N-[1-butyl-4-(4-methoxyphenyl)-1,2-dihydro-2-oxo-1,8-naphthyridin-3-yl]-N'-[2-tert-butyl-5-(1-imidazolylmethyl)phenyl]urea;

N-[1-butyl-4-(3-methyl-2-pyridyl)-1,2-dihydro-2-oxo-1,8-naphthyridin-3-yl]-N'-[2-tert-butyl-5-(1-imidazolylmethyl)phenyl]urea;

N-[1-butyl-4-(3-methoxyphenyl)-1,2-dihydro-2-oxo-1,7-naphthyridin-3-yl]-N'-[2-tert-butyl-5-(1-imidazolylmethyl)phenyl]urea;

N-[1-butyl-4-(3-methoxyphenyl)-1,2-dihydro-2-oxo-1,6-naphthyridin-3-yl]-N'-[2-tert-butyl-5-(1-imidazolylmethyl)phenyl]urea;

N-[1-butyl-4-(3-methoxyphenyl)-1,2-dihydro-2-oxo-1,8-naphthyridin-3-yl]-N'-(2,6-diisopropyl-4-hydroxyphenyl)urea;

N-[1-butyl-4-(3-methoxyphenyl)-1,2-dihydro-2-oxo-1,8-naphthyridin-3-yl]-N'-[2,6-diisopropyl-4-(2-pyridylmethoxy)phenyl]urea;

N-[1-butyl-4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-butyl-4-(3-methoxyphenyl)-1,2-dihydro-2-oxo-1,8-naphthyridin-3-yl]-N'-[2,6-diisopropyl-4-(4-pyridylmethoxy)phenyl]urea;

N-[1-butyl-4-(3-methoxyphenyl)-1,2-dihydro-2-oxo-1,8-naphthyridin-3-yl]-N'-[2,6-diisopropyl-4-[3-(1,2,4-triazol-1-yl)propoxy]phenyl]urea;

N-[1-butyl-4-(3-methoxyphenyl)-1,2-dihydro-2-oxo-1,8-naphthyridin-3-yl]-N'-[2,6-diisopropyl-4-[2-(diethylamino)ethoxyl]-phenyl]urea;

N-[1-butyl-4-(3-methoxyphenyl)-1,2-dihydro-2-oxo-1,8-naphthyridin-3-yl]-N'-[2,6-diisopropyl-4-[2-(morpholino)ethoxy]phenyl]-urea;

N-[1-butyl-4-(3-methoxyphenyl)-1,2-dihydro-2-oxo-1,8-naphthyridin-3-yl]-N'-[2,6-diisopropyl-4-[2-(piperidino)ethoxy]phenyl]-urea;

N-[1-butyl-4-(3-methoxyphenyl)-1,2-dihydro-2-oxo-1,8-naphthyridin-3-yl]-N'-[2,6-diisopropyl-4-[2-(1-pyrrolidinyl)ethoxy]-phenyl]urea;

N-[1-butyl-4-(3-methoxyphenyl)-1,2-dihydro-2-oxo-1,8-naphthyridin-3-yl]-N'-[2,6-diisopropyl-4-[2-(4-methyl-1-piperazinyl)-ethoxy]phenyl]urea;

N-[1-butyl-4-(3-methoxyphenyl)-1,2-dihydro-2-oxo-1,8-naphthyridin-3-yl]-N'-( 2,6-diisopropyl-3-aminophenyl)urea;

N-[1-butyl-4-(3-methoxyphenyl)-1,2-dihydro-2-oxo-1,8-naphthyridin-3-yl]-N'-(2,6-diisopropyl-4-aminophenyl)urea;

N-[1-butyl-4-(3-methoxyphenyl)-1,2-dihydro-2-oxo-1,8-naphthyridin-3-yl]-N'-[2,6-diisopropyl-3-pyridylmethyl)amino]-phenyl]urea;

N-[1-butyl-4-(3-methoxyphenyl)-1,2-dihydro-2-oxo-1,8-naphthyridin-3-yl]-N'-[2,6-diisopropyl-3-[N-(3-pyridylmethyl)-N-methylamino]phenyl]urea;

N-[1-butyl-4-(3-methoxyphenyl)-1,2-dihydro-2-oxo-1,8-naphthyridin-3-yl]-N'-[2,6-diisopropyl-4-(2-pyridylmethyl)amino]-phenyl]urea;

N-[1-butyl-4-(3-methoxyphenyl)-1,2-dihydro-2-oxo-1,8-naphthyridin-3-yl]-N'-[2,6-diisopropyl-4-[N-(3-pyridylmethyl)amino]-phenyl]urea;

N-[1-butyl-4-(3-methoxyphenyl)-1,2-dihydro-2-oxo-1,8-naphthyridin-3-yl]N'-[2,6-diisopropyl-4-[N-(3-pyridylmethyl)-N-methyl-amino]phenyl]urea;

N-[1-butyl-4-(3-methoxyphenyl)-1,2-dihydro-2-oxo-1,8-naphthyridin-3-yl]-N'-[2,6-diisopropyl-4-[N-(4-pyridylmethyl)amino]-phenyl]urea;

N-[1-butyl-4-(3-methoxyphenyl)-1,2-dihydro-2-oxo-1,8-naphthyridin-3-yl]-N'-[2,6-diisopropyl-3-[N-[3-(1,2,4-triazol-1-yl)-propyl]amino]phenyl]urea;

N-[1-butyl-4-(3-methoxyphenyl)-1,2-dihydro-2-oxo-1,8-naphthyridin-3-yl]-N'-[2,6-diisopropyl-4-[N-[3-(1,2,4-triazol-1-yl)-propyl]aminol]phenyl]urea;

N-[4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-methyl-4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-ethyl-4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-propyl-4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-pentyl-4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-(4-pentenyl)-4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-(2-methoxyethyl)-4-(3-methoxyphenyl)-1,2-dihydro-2-oxo-1,8-naphthyridin-3-yl]-N'-[2,6-diisopropyl-4-(3-pyridylmethoxy)phenyl]urea;

N-[1-(3-cyanopropyl)-4-(3-methoxyphenyl)-1,2-dihydro-2-oxo-1,8-naphthyridin-3yl]-N'-[2,6-diisopropyl-4-(3-pyridylmethoxy)phenyl]urea;

N-[1-butyl-4-(6-methyl-2-pyridyl)-1,2-dihydro-2-oxo-1,8-naphthyridin-3-yl]-N'-[2,6-disopropyl-4-(3-pyridylethoxy)phenyl]urea;

N-[1-butyl-4-(3-methoxyphenyl)-1,2-dihydro-2-oxo-1,7-naphthyridin-3-yl]-N'-[2,6-diisopropyl-4-(3-pyridylmethoxy)phenyl]urea;

N-[1-butyl-4-(3-methoxyphenyl)-1,2-dihydro-2-oxo-1,6-naphthyridin-3-yl]-N'-[2,6-diisopropyl-4-(3-pyridylmethoxy)phenyl]urea.

EXAMPLES

The present invention is illustrated in more detail by the following Reference Example and Examples, but should not be construed to be limited thereto.

Example 1

Preparation of N-[1-butyl-4-(3-methoxyphenyl)-1,2-dihydro-2-oxo-1,8-naphthyridin-3yl]-N'-[2-tert-butyl-5-(morpholinomethyl)phenyl]urea:

To a solution of 1-butyl-3-carboxy-4-(3-methoxyphenyl)-1,2-dihydro-2-oxo-1,8-naphthyridine (2.0 g, 5.60 mmol) in DMF (N,N-dimethylformamide, 20 ml) are added DPPA (diphenyl phosphorylazide, 1.87 g, 6.81 mmol) and triethylamine (0.57 g, 5.68 mmol), and the mixture is stirred at room temperature for one hour, and stirred at about 60° C. for 3 hours. To the mixture is added 2-tert-butyl-5-(morpholinomethyl)aniline (1.69 g, 6.81 mmol), and the mixture is stirred at 50–60° C. for 12 hours. To the reaction solution is added water, and the mixture is extracted with ethyl acetate. The extract is washed with water and a saturated brine, and dried over anhydrous magnesium sulfate. The solvent is evaporated under reduced pressure, and the resulting residue is purified by silica gel column chromatography (chloroform to 2% methanol/chloroform) to give the title compound (3.06 g, 5.12 mmol) as colorless oil.

To a solution of the above oil in ethanol (30 ml) is added 1N solution of hydrochloric acid in ether (5.9 ml), and the mixture is concentrated under reduced pressure. To the resulting residue are added isopropanol (10 ml) and ethyl acetate (30 ml), and the mixture is heated to dissolve the residue. The mixture is stirred at room temperature for one hour, and then stirred under ice-cooling for one hour. The precipitated crystals are collected by filtration to give the hydrochloride of the title compound (2.27 g, 3.6 mmol) as colorless crystals.

mp 196–198.5° C. IR (KBr) 2960, 1703, 1634, 1521, 1456, 1288, 1236, 1124 cm$^{-1}$.

Example 2

Preparation of N-[1-(2-methoxyethyl)-4-(3-methoxyphenyl)-1,2-dihydro-2-oxo-1,8-naphthyridin-3-yl]-N'-[2-tert-butyl-5-(morpholinomethyl)-phenyl]urea:

In the same manner as in Example 1, the hydrochloride of the title compound is obtained from 1-(2-methoxyethyl)-3-carboxy-4-(3-methoxyphenyl)-1,2-dihydro-2-oxo-1,8-naphthyridine as colorless crystals.

mp 171–173.5° C. IR (KBr) 2966, 1645, 1585, 1529, 1455, 1245, 1123, 1085, 780 cm$^{-1}$.

Example 3

Preparation of N-[1-(3-cyanopropyl)-4-(3-methoxyphenyl)-1,2-dihydro-2-oxo-1,8-naphthyridin-3-yl]-N'-[2-tert-butyl-5-(morpholinomethyl)-phenyl]urea:

In the same manner as in Example 1, the hydrochloride of the title compound is obtained from 1-(3-cyanopropyl)-3-carboxy-4-(3 methoxyphenyl)-1,2-dihydro-2-oxo-1,8-naphthyridine as colorless crystals.

mp 168–170° C. $^1$H-NMR δ (DMSO-d$_6$) 1.22 (9H, s), 2.06 (2H, m), 2.65 (2H, t, J=7.1 Hz), 3.05 (2H,br), 3.21 (2H, br d, J=12.1 Hz), 3.70 (2H, br), 3.74 (3H, s), 3.92 (2H, br d, J=12.2 2 Hz), 4.21 (2H, br), 4.62 (2H, t, J=6.8 Hz), 7.75 (1H, br), 8.21 (1H, br), 8.61 (1H, br).

Example 4

Preparation of N-[4-(3-methoxyphenyl)-1,2-dihydro-2-oxo-1,8-naphthyridin-3-yl]-N'-[2-tert-butyl-5-(morpholinomethyl)phenyl]urea:

In the same manner as in Example 1, the hydrochloride of the title compound is obtained from 3-carboxy-4-(3-methoxyphenyl)-1,2-dihydro-2-oxo-1,8-naphthyridine as colorless crystals.

mp 176–178° C. $^1$H-NMR δ (DMSO-d$_6$) 1.21 (9H, s), 3.06 (2H, br), 3.23 (2H, br d, J=11.9 Hz), 4.21 (2H,br), 7.19 (1H, dd, J=8.1 Hz, 4.4 Hz), 7.56 (1H, dd, J=8.1 Hz, 1.5 Hz), 8.49 (1H, dd, J=4.4 Hz, 1.5 Hz).

Example 5

Preparation of N-[1-hexyl-4-(3-methoxyphenyl)-1,2-dihydro-2-oxo-1,8-naphthyridin-3-yl]-N'-[2-tert-butyl-5-(morpholinomethyl)phenyl]urea:

To a solution of N-[4-(3-methoxyphenyl)-1,2-dihydro-2-oxo-1,8-naphthyridin-3-yl]-N'-[2-tert-butyl-5-(morpholinomethyl)phenyl]urea (300 mg, 0.55 mmol) in DMF (10 ml) are added successively potassium carbonate (91.8 mg, 0.66 mmol), potassium iodide (18.4 mg, 0.11 mmol) and 1-iodohexane (117 mg, 0.55 mmol), and the mixture is stirred at room temperature for one hour, and stirred at 40–50° C. for 4 hours. The reaction solution is poured into water, and the mixture is extracted with ethyl acetate. The extract is washed with water and a saturated brine, and dried over anhydrous magnesium sulfate. The solvent is concentrated under reduced pressure, and the resulting residue is purified by silica gel column chromatography (chloroform→3% methanol/chloroform) to give the title compound (290 mg, 0.47 mmol) as colorless oil.

To a solution of the above oil in ethanol (3 ml) is added a 1M solution of hydrochloric acid in ether (0.5 ml), and further thereto is added ether. The mixture is stirred at room temperature for one hour, and stirred under ice-cooling for one hour. The precipitated crystals are collected by filtration to give the hydrochloride of the title compound (255 mg, 0.39 mmol) as colorless crystals.

mp 181–182° C. IR(KBr)2961, 1700, 1634, 1583, 1520, 1456, 1236, 1123 cm$^{-1}$.

Example 6

Preparation of N-[1-(4-pentenyl)-4-(3-methoxyphenyl)-1,2-dihydro-2-oxo- 1,8-naphthyridin-3-yl]-N'-[2-tert-butyl-5-(morpholinomethyl)phenyl]urea:

In the same manner as in Example 5, the hydrochloride of the title compound is obtained from N-[4-(3-methoxyphenyl)-1,2-dihydro-2-oxo1,8-naphthyridin-3-yl]-N'-[2-tert-butyl-5-(morpholinomethyl)phenyl]urea and 5-bromo-1-pentene as colorless crystals.

mp 165–168° C. IR (KBr) 2966, 1643, 1584, 1529, 1456, 1244 cm$^{-1}$.

Example 7

Preparation of N-[1-butyl-4-(3-methoxyphenyl)-1,2-dihydro-2-oxo-1,8-naphthyridin-3-yl]-N'-[2-tert-butyl-5-(hydroxymethyl)phenyl]urea:

(a) Preparation of N-[1-butyl-4-(3-methoxyphenyl)-1,2-dihydro-2-oxo-1,8-naphthyridin-3-yl]-N'-[2-tert-butyl-5-[(tetrahydro-2H-pyran-2-yl)oxymethyl]phenyl]urea:

In the same manner as in Example 1, the title compound is obtained from 1-butyl-3-carboxy-4-(3-methoxyphenyl)-1,2-dihydro-2-oxo-1,8-naphthyridine and 2-tert-butyl-5-[(tetrahydro-2H-pyran-2-yl)oxymethyl]aniline. $^1$H-NMR δ (CDCl$_3$) 0.96 (3H, t, J=7.3 Hz), 1.27 (9H, s), 3.53 (1H, m), 3.80 (3H, s), 3.91 (1H, m), 4.40 (1H, d, J=12.1 Hz), 4.56 (2H, t, J=7.7 Hz), 4.70 (1H, d, J=12.1 Hz), 4.70 (1H, m).

(b) Preparation of N-[1-butyl-4-(3-methoxyphenyl)-1,2-dihydro-2-oxo-1,8-naphthyridin-3-yl]-N'-[2-tert-butyl-5-(hydroxymethyl)phenyl]urea:

To a solution of N-[1-butyl-4-(3-methoxyphenyl)-1,2-dihydro-2-oxo-1,8-naphthyridin-3-yl]-N'-[2-tert-butyl-5-[(tetrahydro-2H-pyran-2-yl)-oxymethyl]phenyl]urea (34.05 g, 55.6 mmol) in methanol (340 ml) is added p-toluenesulfonic acid (10.57 g, 55.6 mmol), and the mixture is stirred at room temperature for two hours. Methanol is evaporated under reduced pressure, and to the resultant is added water, and the mixture is extracted with ethyl acetate. The extract is washed with water, an aqueous sodium hydrogen carbonate solution and a saturated brine, and dried over magnesium sulfate. The solvent is evaporated under reduced pressure, and the resulting residue is purified by silica gel column chromatography (ethyl acetate:hexane= 1:1→ethyl acetate:hexane=3:1) to give the title compound (21.6 g, 40.8 mmol). Some of the title compound (2.03 g) is dissolved in ethyl acetate (2 ml), and thereto is added hexane. The mixture is stirred at room temperature for 3 hours, and stirred under ice-cooling for one hour. The precipitated crystals are collected by filtration to give the title compound (1.70 g) as colorless crystals.

mp 102–105° C. IR (KBr) 2959, 1638, 1584, 1527, 1456, 1288, 1247, 1047, 777 cm$^{-1}$.

Example 8

Preparation of N-[1-butyl-4-(3-methoxyphenyl)-1,2-dihydro-2-oxo-1,8-naphthyridin-3-yl]-N'-[2-tert-butyl-5(1-pyrrolidinylmethyl)phenyl]urea:

(a) Preparation of N-[1-butyl-4-(3-methoxyphenyl)-1,2-dihydro-2-oxo-1,8-naphthyridin-3-yl]-N'-[2-tert-butyl-5-(bromomethyl)phenyl]urea:

To a solution of N-[1-butyl-4-(3-methoxyphenyl)-1,2-dihydro-2-oxo-1,8-naphthyridin-3-yl]-N'-[2-tert-butyl-5-(hydroxymethyl)phenyl]urea (13.99 g, 26.5 mmol) in methylene chloride (140 ml) are added triphenylphophine (8.36 g, 31.76 mmol.) and carbon tetrabromide (13.16 g, 39.7 mmol), and the mixture is stirred at room temperature for 2 hours. To the mixture is added water, and the mixture is extracted with methylene chloride. The extract is washed with water, an aqueous sodium hydrogen carbonate solution and a saturated brine, and dried over anhydrous magnesium sulfate. The solvent is concentrated under reduced pressure, and the resulting residue is purified by silica gel column chromatography (ethyl acetate:hexane=1:2). To the resulting concentrated product is added a mixed solvent of ether and hexane (1:1), and the mixture is stirred at room temperature for 3 hours, and then stirred under ice-cooling for one hour. The precipitated crystals are collected by filtration to give the title compound (9.96 g, 16.8 mmol) as pale yellow crystals.

IR (KBr) 2959, 1643, 1584, 1530, 1455, 1246 cm$^-$.
$^1$H-NMR δ (CDCl$_3$) 0.98 (3H, t, J=7.3 Hz), 1.31 (9H, s), 3.84 (3H, s), 4.42 (2H, s), 4.59 (2H, t, J=7.7 Hz).

(b) Preparation of N-[-butyl-4-(3-methoxyphenyl)-1,2-dihydro-2-oxo-1,8-naphthyridin-3-yl]-N'-[2-tert-butyl-5-(1-pyrrolidinylmethyl)phenyl]urea:

To a solution of N-[1-butyl-4-(3-methoxyphenyl)-1,2-dihydro-2-oxo-1,8-naphthyridin-3-yl]-N'-[2-tert-butyl-5-(bromomethyl)phenyl]urea (330 mg, 0.56 mmol) in THF (tetrahydrofuran, 5 ml) is added pyrrolidine (362 mg, 5.09 mmol), and the mixture is stirred at room temperature for 3 hours. The mixture is poured into water, and the mixture is extracted with ethyl acetate. The extract is washed with water and a saturated brine, and dried over anhydrous magnesium sulfate. The solvent is evaporated under reduced pressure, and the resulting residue is purified by silica gel column chromatography (5–10% methanol/chloroform) to give the title compound (234 mg, 0.42 mmol) as colorless oil.

To a solution of the above oil in ethanol (5 ml) is added a 1M solution of hydrochloric acid in ether (0.6 ml), and the mixture is concentrated under reduced pressure. To the resulting residue is added ether (30 ml), and the mixture is stirred at room temperature for one hour, and stirred under ice-cooling for one hour. The precipitated crystals are collected by filtration to give the hydrochloride of the title compound (194 mg, 0.39 mmol) as colorless crystals.

mp 150–156° C. IR (KBr) 2961, 1642, 1584, 1530, 1455, 1247, 1044, 779 cm$^{-1}$.

Example 9

Preparation of N-[1-butyl-4-(3-methoxyphenyl)-1,2-dihydro-2-oxo-1,8-naphthyridin-3-yl]-N'-[2-tert-butyl-5-(piperidinomethyl)phenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-butyl-5-(bromomethyl)phenyl]urea and piperidine.

mp 153–157° C. IR (KBr) 2959, 1643, 1584, 1530, 1455, 1246 cm$^{-1}$.

Example 10
Preparation of N-[1-butyl-4-(3-methoxyphenyl)-1,2-dihydro-2-oxo-1,8-naphthyridin-3-yl]-N'-[2-tert-butyl-5-(dipropylaminomethyl)phenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-butyl-5-(bromomethyl)phenyl]urea and dipropylamine.

mp 194.5–197° C. IR (KBr) 2965, 1642, 1585, 1528, 1455, 1425, 1252, 1043, 780 cm$^{-1}$.

Example 11
Preparation of N-[1-butyl-4-(3-methoxyphenyl)-1,2-dihydro-2-oxo-1,8-naphthyridin-3-yl]-N'-[2-tert-butyl-5-(diethylaminomethyl)phenyl]urea:

In the same manner as in Example 8 (b), the hydrochloride of the title compound is obtained from N-[1-butyl-4-(3-methoxyphenyl)-1,2-dihydro-2-oxo- 1,8-naphthyridin-3-yl]-N'-[2-tert-butyl-5-(bromomethyl)phenyl]urea and diethylamine.

mp 159–161° C. IR (KBr) 2960, 1642, 1585, 1525, 1455, 1425, 1252, 1042, 780 cm$^{-1}$.

Example 12
Preparation of N-[1-butyl-4-(3-methoxyphenyl)-1,2-dihydro-2-oxo-1,8-naphthyridin-3-yl]-N'-[2-tert-butyl-5-(4-methylpiperazin-1-yl)methyl]-phenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-butyl-5-(bromomethyl)-phenyl]urea and 1-methylpiperazine.

mp 168–171.5° C. IR (KBr) 2961, 1640, 1585, 1530, 1455, 1427, 1247, 1046, 779 cm$^{-1}$.

Example 13
Preparation of N-[1-butyl-4-(3-methoxyphenyl)-1,2-dihydro-2-oxo-1,8-naphthyridin-3-yl]-N'-[2-tert-butyl-5-(2-pyridylmethyl)aminomethylphenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-butyl-5-(bromomethyl)-phenyl]urea and 2-aminomethylpyridine.

mp 158–161° C. IR (KBr) 2962, 1641, 1485, 1530, 1455, 1426, 1246, 1042, 777 cm$^{-1}$.

Example 14
Preparation of N-[1-butyl-4-(3-methoxyphenyl)-1,2-dihydro-2-oxo-1,8-naphthyridin-3yl]-N'-[2-tert-butyl-5-(3-pyridylmethyl)aminomethylphenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-butyl-5-(bromomethyl)-phenyl]urea and 3-aminomethylpyridine.

mp 142–147.5° C. IR (KBr) 2961, 1640, 1584, 1530, 1455, 1426, 1247, 1044, 780 cm$^{-1}$.

Example 15
Preparation of N-[1-butyl-4-(3-methoxyphenyl)-1,2-dihydro-2-oxo-1,8-naphthyridin-3-yl]-N'-[2-tert-butyl-5-(4-pyridylmethyl)aminomethylphenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-butyl-5-(bromomethyl)-phenyl]urea and 4-aminomethylpyridine.

mp 153–157° C. IR (KBr) 2961, 1640, 1584, 1530, 1455, 1426, 1248, 1044, 780 cm$^{-1}$.

Example 16
Preparation of N-[1-butyl-4-(3-methoxyphenyl)-1,2-dihydro-2-oxo-1,8-naphthyridin-3-yl]-N'-[2-tert-butyl-5-[N-(2-pyridylmethyl)-N-methyl aminomethyl]phenyl]urea:

To a solution of N-[1-butyl-4-(3-methoxyphenyl)-1,2-dihydro-2-oxo-1,8-naphthyridin-3-yl]-N'-[2-tert-buthyl-5-(2-pyridylmethyl)aminomethylphenyl]urea (400 mg, 0.65 mmol) in methanol (5 ml) are added successively conc. hydrochloric acid (0.11 ml, 1.3 mmol), a 37% solution of formaldehyde in methanol (63 mg, 0.78 mmol), sodium borohydride (49 mg, 0.78 mmol) under ice-cooling, and the mixture is stirred at the same temperature for one hour, and then stirred at room temperature for 3 hours. The mixture is poured into an aqueous sodium hydrogen carbonate solution, and the mixture is extracted with ethyl acetate. The extract is washed with water and a saturated brine, and dried over anhydrous magnesium sulfate. The solvent is concentrated under reduced pressure, and the resulting residue is purified by silica gel column chromatography (chloroform →3% methanol/chloroform) to give the title compound (255 mg, 0.40 mmol) as colorless oil.

To a solution of the above oil in ethanol (5 ml) is added a 1 M solution of hydrochloric acid in ether (1.0 ml), and the mixture is concentrated under reduced pressure. To the resulting residue is added ether (30 ml), and the mixture is stirred at room temperature for one hour, and then stirred under ice-cooling for one hour. The precipitated crystals are collected by filtration to give the hydrochloride of the title compound (234 mg, 0.33 mmol) as colorless crystals.

mp 124–128° C. $^1$H-NMR δ (DMSO-d$_6$) 0.97 (3 H, t, J=7.3 Hz), 1.22 (9H, s), 2.67 (3H, s), 3.73 (3H, s), 6.86–6.89 (2H, m), 7.80 (1H, s), 8.68 (1H, d, J=4.8 Hz).

Example 17
Preparation of N-[1-butyl-4-(3-methoxyphenyl)-1,2-dihydro-2-oxo-1,8-naphthyridin-3-yl]-N'-[2-tert-buthyl-5-[N-(3-pyridymithyl)-N-methyl aminomethyl]phenyl]urea:

In the same manner as in Example 16, the hydrochloride of the title compound is obtained from N-[1-butyl-4-(3-methoxyphenyl)-1,2-dihydro-2-oxo-1,8-naphthyridin-3-yl]-N'-[2-tert-butyl-5-[N-(3-pyridylmethyl)aminomethyl]phenyl]urea and formaldehyde as colorless crystals.

mp 158–162.5° C. IR (KBr) 2959, 1638, 1584, 1531, 1425, 1249, 1045, 780, 686 cm$^{-1}$.

Example 18
Preparation of N-[1-butyl-4-(3-methoxyphenyl)-1,2-dihydro-2-oxo-1,8-naphthyridin-3-yl]-N'-[2-tert-butyl-5-[N-(4-pyridylmethyl)-N-methylaminomethyl]phenyl]urea:

In the same manner as in Example 16, the hydrochloride of the title compound is obtained from N-[1-butyl-4-(3-methoxyphenyl)-1,2-dihydro-2-oxo-1,8-naphthyridin-3-yl]-N'-[2-tert-butyl-5-[N-(4-pyridylmethyl)aminomethyl]phenyl]urea and formaldehyde as colorless crystals.

mp 160–164° C. IR (KBr) 2961, 1640, 1584, 1456, 1424, 1249, 1046, 781 cm$^{-1}$.

Example 19
Preparation of N-[1-butyl-4-(3-methoxyphenyl)-1,2-dihydro-2-oxo-1,8-naphthyridin-3-yl]-N'-[2-tert-butyl-5-(1-pyrazolylmethyl)phenyl]urea:

In the same manner as in Example 8 (b), the title compound is prepared from N-[1-butyl-4-(3-methoxyphenyl)-1,2-dihydro-2-oxo-1,8-naphthyridin-3-yl]-N'-[2-tert-butyl-5-(bromomethyl)phenyl]urea and pyrazole.

$^1$H-NMR δ (DMSO-$d_6$) 0.97 (3H, t, J=7.3 Hz), 1.17 (9H, s), 3.73 (3H, s), 4.51 (2H, t, J=7.5 Hz), 5.19 (2H, s), 6.96 (1H, d, J=9.2 Hz), 7.20–7.27 (2H, m), 7.36 (1H, dd, J=8.1 Hz, 7.9 Hz), 7.41 (1H, d, J=1.7 Hz), 7.74 (1H, d, J=1.8 Hz), 8.06 (1H, s), 8.61 (1H, dd, J=4.8 Hz, 1.7 Hz).

Example 20

Preparation of N-[1-butyl-4-(3-methoxyphenyl)-1,2-dihydro-2-oxo-1,8-naphthyridin-3-yl]-N'-[2-tert-buthyl-5]-(3,5-dimethylpyrazol-1-yl)-methyl]phenyl]urea:

In the same manner as in Example 8 (b), the title compound is obtained from N-[1-butyl-4-(3-methoxyphenyl)-1,2-dihydro-2-oxo-1,8-naphthyridin-3-yl]-N'-[2-tert-buthyl-5-(bromomethyl)phenyl]urea and 3,5-dimethylpyrazole.

IR (KBr) 2961, 1645, 1584, 1529, 1424, 1251, 1045, 780 cm$^{-1}$.

Example 21

Preparation of N-[1-butyl-4-(3-methoxyphenyl)-1,2-dihydro-2-oxo-1,8-naphthyridin-3-yl]-N'-[2-tert-buthyl-5-(1-imidazolylmethylphenyl)urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-buthyl-5-(bromomethyl)-phenyl]urea and imidazole.

mp 151–154° C. $^1$H-NMR δ (DMSO-$d_6$) 0.97 (3H, t, J=7.3 Hz), 1.18 (9H, s), 3.72 (3H, s), 4.51 (2H, t, J=7.4 Hz), 5.31 (2H, s), 7.62 (1H, dd, J=7.9 Hz, 1.7 Hz), 7.76 (1H, dd, J=1.7 Hz, 1.5 Hz), 7.67 (2H, br s), 8.21 (1H, s), 8.61 (1H, dd, J=4.6 Hz, 1.8 Hz), 9.23 (1H, s).

Example 22

Preparation of N-[1-butyl-4-(3-methoxyphenyl)-1,2-dihydro-2-oxo-1,8-naphthyridin-3-yl]-N'-[2-tert-buthyl-5-[(2-methylimidazol-1-yl)methyl]phenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-buthyl-5-(bromomethyl)-phenyl]urea and 2-methylimidazole.

mp 183–185° C. IR (KBr) 2961, 1639, 1600, 1539, 1455, 1425, 1288, 1251, 1046, 778 cm$^{-1}$.

Example 23

Preparation of N-1-butyl-4-(3-methoxyphenyl)-1,2-dihydro-2-oxo-1,8-naphthyridin-3-yl]-N'-[2-tert-buthyl-5-[(1,2,4-triazol-1-yl)methyl]phenyl]urea:

In the same manner as in Example 8 (b), the hydrochloride of the title compound is obtained from N-[1-butyl-4-(3-methoxyphenyl)-1,2-dihydro-2-oxo-1,8-naphthyridin-3-yl]-N'-[2-tert-butyl-5-(bromomethyl)-phenyl]urea and 1,2,4-triazole.

mp 139–140° C. IR (KBr) 2960, 1639, 1584, 1534, 1456, 1425, 1287, 1250, 1048, 778 cm$^{-1}$.

Example 24

Preparation of N-[1-butyl-4-(3-methoxyphenyl)-1,2-dihydro-2-oxo-1,8-naphthyridin-3-yl]-N'-(2,6-diisopropyl-4-hydroxyphenyl)urea:

(a) Preparation of N-[1-butyl-4-(3-methoxyphenyl)-1,2-dihydro-2-oxo-1,8-naphthyridin-3-yl]-N'-[2,6-diisopropyl-4-(3-chlorobenzoylxy)-phenyl]urea:

To a solution of 3-amino-1-butyl-4-(3-methoxyphenyl)-1,2-dihydro-2-oxo-1,8-naphthyridine (2.14 g, 6.63 mmol) in tetrahydrofuran (20 ml) is added phenyl chlorocarbonate (1.66 ml, 13.2 mmol), and the mixture is stirred at 40–50° C. for 3 hours. After allowed to cool, water is added to the mixture, and the mixture is extracted with ethyl acetate. The extract is washed with a 5% aqueous brine, and dried over anhydrous magnesium sulfate, and concentrated under reduced pressure. The resulting residue is dissolved in dimethylformamide (30 ml), and thereto are added dropwise successively a solution of 2,6-diisopropyl-4-(3-chlorobenzoyloxy)aniline (2.0 g, 6.03 mmol) in dimethylformamide (5 ml), and a solution of 4-dimethylaminopyridine (0.74 g, 12 mmol) in dimethylformamide (5 ml) at room temperature. The mixture is stirred at room temperature for 8 hours, and to the reaction solution is added water. The mixture is extracted with ethyl acetate. The extract is washed successively with an aqueous ammonium chloride solution, an aqueous sodium hydrogen carbonate solution, and a saturated brine, dried over anhydrous magnesium sulfate, and concentrated under reduced pressure. The resulting residue is purified by silica gel column chromatography (ethyl acetate:hexane=1:5→ethyl acetate:hexane=1:2) to give the title compound (2.1 g, 3.35 mmol) as amorphous.

$^1$H-NMR δ (DMSO-$d_6$) 0.98 (3H, t, J=7.3 Hz), 3.79 (3H, s), 4.53 (2H, t, J=7.3 Hz), 7.03 (1H, dd, J=5.7 Hz, 2.4 Hz), 7.25 (1H, dd, J=7.9 Hz, 4.6 Hz), 7.43 (1H, t, J=8.1 Hz), 7.61–7.66 (2H, m), 7.78–7.82 (3H, m), 8.06–8.10 (2H, m).

(b) Preparation of N-[1-butyl-4-(3-methoxyphenyl)-1,2-dihydro-2-oxo-1,8-naphthyridin-3-yl]-N'-(2,6-diisopropyl-4-hydroxyphenyl)urea:

To a solution of N-[1-butyl-4-(3-methoxyphenyl)-1,2-dihydro-2-oxo-1,8-naphthyridin-3-yl]-N'-[2,6-diisopropyl-4-(3-chlorobenzoyloxy)-phenyl]urea (1.0 g, 1.6 mmol) in methanol (30 ml) is added dropwise a 28% sodium methoxide (0.45 ml, 1.76 mmol) at room temperature, and the mixture is stirred at the same temperature for one hour. To the mixture is added water, and the mixture is extracted with ethyl acetate. The extract is washed with an aqueous ammonium chloride solution and a saturated brine, dried over anhydrous magnesium sulfate, and concentrated under reduced pressure. The resulting residue is purified by silica gel column chromatography (1% methanol/chloroform→2% methanol/chloroform) to give the title compound (0.79 g, 1.45 mmol) as amorphous.

$^1$H-NMR δ (DMSO-$d_6$) 3.77 (3H, s), 4.52 (2H, t, J=7.7 Hz), 7.01 (1H, dd, J=8.0 Hz, 2.4 Hz), 7.24 (1H, dd, J=8.1 Hz, 4.6 Hz), 7.40 (1H, t, J=8.0 Hz), 7.50 (1H, s), 7.62 (1H, dd, J=7.9 Hz, 1.5 Hz), 7.67 (1H, s), 8.60 (1H, dd, J=4.8 Hz, 1.7 Hz), 9.05 (1H, s).

Example 25

Preparation of N-[1-butyl-4-(3-methoxyphenyl)-1,2-dihydro-2-oxo-1,8-naphthyridin-3-yl]-N'-[2,6-diisopropyl-4-(3-piperdinopropoxy)-phenyl]urea:

To a solution of N-[1-butyl-4-(3-methoxyphenyl)-1,2-dihydro-2-oxo-1,8-naphthyridin-3-yl]-N'-(2,6-diisopropyl-4-hydroxyphenyl)urea(254 mg, 0.47 mmol) in DMF (7 ml) are added successively potassium carbonate (193 mg, 1.40 mmol), potassium iodide (39 mg, 0.23 mmol), 1-(3-chloropropyl)piperidine hydrochloride (111 mg, 0.56 mmol) at room temperature, and the mixture is stirred at about 45° C. for 5 hours. To the mixture is added water, and the mixture is extracted with ethyl acetate. The extract is washed with water and a saturated brine, dried over anhydrous magnesium sulfate, and concentrated under reduced pressure. The resulting residue is purified by silica gel column chromatography (ethyl acetate:hexane=3:2→3% ethanol/ ethyl acetate) to give the title compound (168 mg, 0.25 mmol) as amorphous.

To a solution of the above amorphous in ethyl acetate (1 ml) is added a 1M hydrochloric acid in ether (0.5 ml), and thereto is further added ether (20 ml). The mixture is stirred at room temperature for one hour, and then stirred under ice-cooling for one hour. The precipitated crystals are collected by filtration to give the hydrochloride of the title compound (153 mg, 0.22 mmol) as colorless crystals.

$^1$H-NMR δ (CD$_3$OD) 1.01 (3H, t, J=7.3 Hz), 2.78–3.00 (2H, m), 3.82 (3H, s), 3.96 (2H, t, J=6.0 Hz), 4.61 (2H, t, J=7.5 Hz), 6.60 (2H, s), 7.18 (1H, dd, J=8.1 Hz, 4.6 Hz), 7.71 (1H, dd, J=6.2 Hz, 1.7 Hz), 8.58 (1H, dd, J=4.6 Hz, 1.8 Hz).

Example 26
Preparation of N-[1-butyl-4-(3-methoxyphenyl)-1,2-dihydro-2-oxo-1,8-naphthyridin-3-yl]-N'-[2,6-diisopropyl-4-(2-piperidinoethoxy) phenyl]-urea:

In the same manner as in Example 25, the hydrochloride of the title compound is obtained from N-[1-butyl-4-(3-methoxyphenyl)-1,2-dihydro-2-oxo-1,8-naphthyridin-3-yl]-N'-(2,6-diisopropyl-4-hydroxyphenyl)urea and 1-(2-chloroethyl)piperidine hydrochloride as colorless crystals.

$^1$H-NMR δ (CD$_3$OD) 1.00 (3H, t, J=7.1 Hz), 2.90–2.98 (2H, m), 3.82 (3H, s), 4.07 (2H, t, J=5.7 Hz), 4.60 (2H, t, J=7.5 Hz), 6.63 (2H, s), 7.17 (1H, dd, J=8.1 Hz, 4.6 Hz), 7.70 (1H, dd, J=7.9 Hz, 1.7 Hz), 8.57 (1H, dd, J=4.6 Hz, 1.8 Hz).

Example 27
Preparation of N-[1-butyl-4-(3-methoxyphenyl)-1,2-dihydro-2-oxo-1,8-naphthyridin-3-yl]-N'-[2,6-2,6-diisopropyl-4-(3-pyridylmethoxy)phenyl]urea:

In the same manner as in Example 25, the hydrochloride of the title compound is obtained from N-[1-butyl-4-(3-methoxyphenyl)-1,2-dihydro-2-oxo-1,8-naphthyridin-3-yl]-N'-(2,6-diisopropyl-4-hydroxyphenyl)urea and 3-picolyl chloride hydrochloride as colorless crystals.

$^1$H-NMR δ (CD$_3$OD) 1.00 (3H, t, J=7.3 Hz), 2.89–2.98 (2H, m), 3.81 (3H, s), 4.61 (2H, t, J=7.5 Hz), 5.11 (2H, s), 6.70 (2H, s), 7.18 (1H, dd, J=8.1 Hz, 4.7 Hz), 7.70 (1H, dd, J=8.1 Hz, 1.8 Hz), 7.91 (1H, d, J=7.9 Hz), 8.46 (1H, d, J=3.5 Hz), 8.58 (1H, dd, J=4.6 Hz, 1.8 Hz), 8.61 (1H, s).

Example 28
Preparation of N-[1-butyl-4-(3-methoxyphenyl)-1,2-dihydro-2-oxo-1,8-naphthyridin-3-yl]-N'-[2,6-diisopropyl-4-[3-(1,2,4-triazol-1-yl)propoxy]-phenyl]urea:

In the same manner as in Example 25, the hydrochloride of the title compound is obtained from N-[1-butyl-4-(3-methoxyphenyl)-1,2-dihydro-2-oxo-1,8-naphthyridin-3-yl]-N'-(2,6-diisopropyl-4-hydroxyphenyl)urea and 1-(3-bromopropyl)-1,2,4-triazole as colorless crystals.

$^1$H-NMR δ (DMSO-d$_6$) 3.77 (3H, s), 6.53 (2H, s), 7.24 (1H, dd, J=8.0 Hz, 4.8 Hz), 7.40 (1H, dd, J=7.6 Hz, 7.6 Hz), 7.59 (1H, s), 7.62 (1H, d, J=6.4 Hz), 7.69 (1H, s), 7.96 (1H, s), 8.52 (1H, s), 8.61 (1H, d, J=4.6 Hz).

Example 29
Preparation of N-[1-(4-pentenyl)-4-(3-methoxyphenyl)-1,2-dihydro-2-oxo-1,8-naphthyridin-3-yl]-N'-[2-tert-butyl-5-(hydroxymethyl)phenyl]-urea:

In the same manner as in Example 7, the title compound is obtained from 1-(4-pentenyl)-3-carboxy4-(3-methoxyphenyl)-1,2-dihydro-2-oxo-1,8-naphthyridin and 2-tert-butyl-5-[(tetrahydro-2H-pyran-2-yl)oxymethyl] aniline.

IR (KBr) 2962, 1641, 1584, 1530, 1456, 1287, 1244, 1044, 913, 779 cm$^{-1}$.

Examples 30–36

The compounds as listed in Table 1 are obtained in the same manner as in Example 8 (b).

TABLE 1

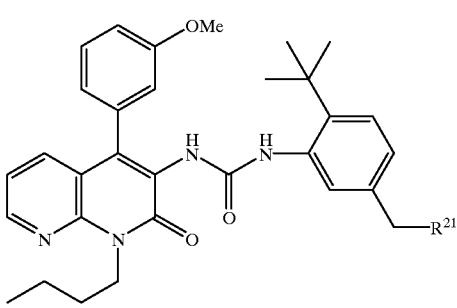

| Ex. No. | R$^{21}$ | Physicochemical properties |
|---|---|---|
| 30 | NMe$_2$ | Hydrochloride: mp 174–175° C. |
| 31 | NHMe | Hydrochloride: mp 163–165° C. |
| 32 | NHEt | Hydrochloride: mp 158–161° C. |
| 33 | NHCHMe$_2$ | Hydrochloride: mp 162–164° C. |
| 34 | NH(CH$_2$)$_2$OH | Hydrochloride: mp 118–123° C. |
| 35 | 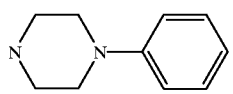 | Hydrochloride: mp 158–168° C. |
| 36 | | Hydrochloride: mp 153–156° C. |

Examples 37 to 40

The compounds as listed in Table 2 are obtained in the same manner as in Example 1.

TABLE 2

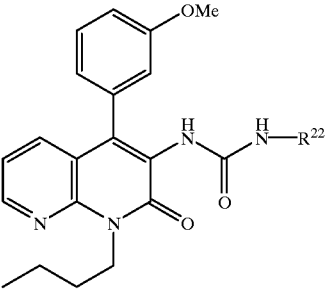

| Ex. No. | R²² | Physical Properties |
|---|---|---|
| 37 | 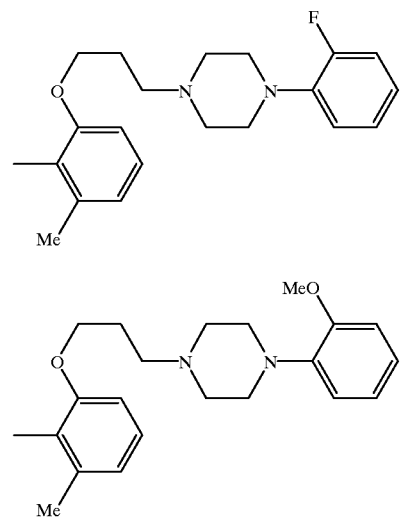 | Hydrochloride: mp 158–168° C. |
| 38 | 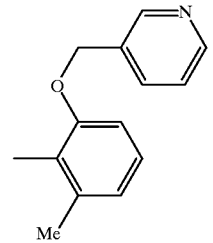 | Hydrochloride: mp 205–207° C. |
| 39 | 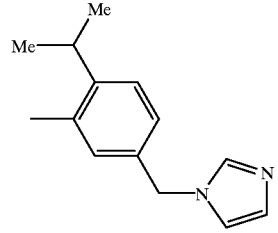 | mp 130–135° C. |
| 40 |  | Hydrochloride: mp 135–143° C. |

Example 41

Preparation of N-[1-butyl-4-(3-methoxyphenyl)-1,2-dihydro-2-oxo-1,8-naphthyridin-3-yl]-N'-(2,6-diisopropyl-4-hydroxymethylphenyl)urea:

(a) Preparation of N-[1-butyl-4-(3-methoxyphenyl)-1,2-dihydro-2-oxo-1,8-naphthyridin-3-yl]-N'-[2,6-diisopropyl-4-(tert-butyldimethylsilyloxymethyl)phenyl]urea:

In the same manner as in Example 24 (a), the title compound is obtained from 3-amino-1-butyl-4-(3-methoxyphenyl)-1,2-dihydro-2-oxo-1,8-naphthyridine and 2,6-diisopropyl-4-(tert-butyldimethylsilyloxymethyl) aniline.

¹H-NMR δ (DMSO-$d_6$) 0.00 (6H, s), 0.84 (9H, s), 3.71 (3H, s), 4.62 (2H, t, J=6.8 Hz), 4.58 (2H, s).

(b) Preparation of N-[1-butyl-4-(3-methoxyphenyl)-1,2-dihydro-2-oxo-1,8-naphthyridin-3-yl]-N'-(2,6-diisopropyl-4-hydroxymethylphenyl)urea:

A solution of N-[1-butyl-4-(3-methoxyphenyl)-1,2-dihydro-2-oxo-1,8-naphthyridin-3-yl]-N'-[2,6-diisopropyl-4-(tert-butyldimethylsilyloxymethyl)phenyl]urea (6.75 g, 10.1 mmol) in methanol containing 15% HCl (100 ml) is stirred at room temperature for 3 hours. Water is added to the reaction solution, and the mixture is extracted with ethyl acetate. The organic layer is washed with water (once) and an aqueous sodium hydrogen carbonate solution (once). The solvent is concentrated under reduced pressure, and the residue is purified by silica gel chromatography to give the title compound (5.0 g, 8.99 mmol) as colorless amorphous.

mp 122–123° C. $^1$H-NMR δ (DMSO-d$_6$) 0.94–1.01 (15H, m), 3.76 (3H, s), 4.40 (2H, d, J=5.7 Hz), 4.51 (2H, t, J=7.1 Hz).

Example 42
Preparation of N-[1-butyl-4-(3-methoxyphenyl)-1,2-dihydro-2-oxo-1,8-naphthyridin-3-yl]-N'-(2,6-diisopropyl-4-aminomethylphenyl)urea:
(a) Preparation of N-[1-butyl-4-(3-methoxyphenyl)-1,2-dihydro-2-oxo-1,8-naphthyridin-3-yl]-N'-(2,6-diisopropyl-4-bromomethylphenyl)urea:

To a solution of N-[1-butyl-4-(3-methoxyphenyl)-1,2-dihydro-2-oxo-1,8-naphthyridin-3-yl]-N'-(2,6-diisopropyl-4-hydroxymethylphenyl)urea (5.0 g, 9.0 mmol) in methylene chloride (50 ml) is added phosphorous tribromide (1.02 ml, 1.10 mmol) under ice-cooling, and the mixture is stirred at room temperature for 4 hours. To the mixture is added water, and the mixture is extracted with ethyl acetate. The organic layer is washed twice with water, and dried over anhydrous magnesium sulfate. The solvent is concentrated under reduced pressure, and the residue is purified by silica gel column chromatography to give the title compound (2.15 g, 4.05 mmol) as colorless amorphous.

$^1$H-NMR δ (DMSO-d$_6$) 0.84–1.02 (15H, m), 3.77 (3H, s), 4.51 (2H, t, J=6.8 Hz), 4.63 (2H, s).
(b) Preparation of N-[1-butyl-4-(3-methoxyphenyl)-1,2-dihydro-2-oxo-1,8-naphthyridin-3-yl]-N'-(2,6-diisopropyl-4-phthalimidomethylphenyl)-urea:

To a solution of N-[1-butyl-4-(3-methoxyphenyl)-1,2-dihydro-2-oxo-1,8-naphthyridin-3-yl]-N'-(2,6-diisopropyl-4-bromomethylphenyl)urea (400 mg, 0.65 mmol) in dimethylformamide (10 ml) is added potassium phthalimide (144 mg, 0.78 mmol) at room temperature, and the mixture is stirred at room temperature for 3 hours. To the mixture is added water, and the mixture is extracted with ethyl acetate. The organic layer is washed twice with water, and dried over anhydrous magnesium sulfate. The solvent is concentrated under reduced pressure, and the residue is purified by silica gel column chromatography to give the title compound (393 mg, 0.57 mmol) as colorless amorphous.

$^1$H-NMR δ (DMSO-d$_6$) 0.93–0.97 (15H, m), 3.75 (3H, s), 4.49 (2H, t, J=6.9 Hz), 7.72 (2H, d, J=5.5 Hz).
(c) Preparation of N-[1-butyl-4-(3-methoxyphenyl)-1,2-dihydro-2-oxo-1,8-naphthyridin-3-yl]-N'-(2,6-diisopropyl-4-aminomethylphenyl)urea:

To a solution of N-[1-butyl-4-(3-methoxyphenyl)-1,2-dihydro-2-oxo-1,8-naphthyridin-3-yl]-N'-(2,6-diisopropyl-4-phthalimidomethylphenyl)-urea (393 mg, 0.57 mmol) in a mixed solvent of ethanol/chloroform (10 ml) is added hydrazine monohydrate (0.033 ml, 0.68 mmol) at room temperature, and the mixture is stirred at room temperature for 2 hours. To the mixture is further added hydrazine monohydrate (0.14 ml, 3.4 mmol), and the mixture is stirred at room temperature for 4 days. To the mixture is added water, and the mixture is extracted with ethyl acetate. The organic layer is washed twice with an aqueous sodium hydrogen carbonate solution, and dried over anhydrous magnesium sulfate. The solvent is concentrated under reduced pressure, and the residue is purified by silica gel column chromatography to give the title compound (256 mg, 0.46 mmol).

$^1$H-NMR δ (DMSO-d$_6$) 0.86–1.01 (15H, m), 3.65 (2H, s), 3.76 (3H, s), 4.51 (2H, t, J=7.0 Hz). Hydrochloride: mp 186–187° C.

Examples 43–45

The compounds as listed in Table 3 are obtained in the same manner as in Example 42 (b).

TABLE 3

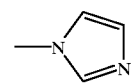

| Ex. No. | R$^{23}$ | Physiochemical properties |
|---|---|---|
| 43 | 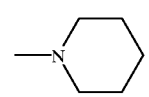 | Hydrochloride: mp 237–238° C. |
| 44 | —N(piperidinyl) | Hydrochloride: mp 257–258° C. |
| 45 | —NEt$_2$ | Hydrochloride: mp 213–214° C. |

Example 46
Preparation of N-[1-butyl-4-(4-methoxyphenyl)-1,2-dihydro-2-oxo-1,8-naphthyridin-3-yl]-N'-[2-tert-butyl-5-(hydroxymethyl)phenyl]urea:

In the same manner as in Example 7, the title compound is obtained from 1-butyl-3-carboxy-4-(4-methoxyphenyl)-1,2-dihydro-2-oxo-1,8-naphthyridine and 2-tert-butyl-5-[(tetrahydro-2H-pyran-2-yl)oxymethyl]aniline.

$^1$H-NMR δ (DMSO-d$_6$) 0.98 (3H, t, J=7.3 Hz), 1.21 (9H, s), 3.79 (3H, s), 4.37 (2H, s), 5.05 (1H, br s), 6.88 (1H, s).

Example 47
Preparation of N-[1-butyl-4-(4-methoxyphenyl)-1,2-dihydro-2-oxo-1,8-naphthyridin-3-yl]-N'-[2-tert-butyl-5-(diethylaminomethyl)phenyl]urea:

In the same manner as in Example 8, the title compound is obtained from N-[1-butyl-4-(4-methoxyphenyl)-1,2-dihydro-2-oxo-1,8-naphthyridin-3-yl]-N'-[2-tert-butyl-5-(hydroxymethyl)phenyl]urea.

Hydrochloride: mp 198–199° C.

Example 48
Preparation of N-[1-butyl-4-(3-methoxyphenyl)-1,2-dihydro-2-oxo-1,8-naphthyridin-3-yl]-N'-[2-tert-butyl-5-(aminomethyl)phenyl]urea:

To a solution of N-[1-butyl-4-(3-methoxyphenyl)-1,2-dihydro-2-oxo-1,8-naphthyridin-3-yl]-N'-[2-tert-butyl-5-

(bromomethyl)phenyl]urea (400 mg, 0.68 mmol) in dimethylformamide (20 ml) is added sodium azide (440 mg, 6.76 mmol), and the mixture is stirred at about 60° C. for 8 hours. To the mixture is added water, and the mixture is extracted with ethyl acetate. The organic layer is washed twice with water, and dried over anhydrous magnesium sulfate. The residue is purified by silica gel column chromatography to give the colorless solid.

A suspension of the above solid, conc. hydrochloric acid (0.095 ml, 1.14 mmol) and palladium carbon (180 mg) in methanol (10 ml) is stirred under hydrogen atmosphere for 5 hours. Then, the mixture is filtered on celite, and the solvent was evaporated. The resultant is extracted with ethyl acetate, and the organic layer is washed twice with an aqueous sodium hydrogen carbonate solution, and dried over anhydrous magnesium sulfate. The solvent is concentrated under reduced pressure, and the residue is purified by silica gel column chromatography to give the title compound (344 mg, 0.65 mmol) as colorless amorphous.

$^1$H-NMR δ (DMSO-$d_6$) 0.98 (3H, t, J=7.3 Hz), 1.20 (9H, s), 2.11 (2H, br), 3.60 (2H, s), 3.74 (3H, s), 7.63 (1H, s), 8.03 (1H, s).

Example 49

Preparation of N-[1-butyl-4-[3-(3-pyridylmethoxy)phenyl]-1,2-dihydro-2-oxo-1,8-naphthyridin-3-yl]-N'-[2-tert-butyl-5-(hydroxymethyl)phenyl]urea:

In the same manner as in Example 24 (a), N-[1-butyl-4-[3-(3-pyridylmethoxy)phenyl]-1,2-dihydro-2-oxo-1,8-naphthyridin-3-yl]-N'-[2-tert-butyl-5-[(tetrahydro-2H-pyran-2-yl)oxymethyl]phenyl]urea is obtained from 3-amino-1-butyl-4-[3-(3-pyridylmethoxy)phenyl]-1,2-dihydro-2-oxo-1,8-naphthyidine and 2-tert-butyl-5-[(tetrahydro-2H-pyran-2-yl)oxymethyl]aniline.

$^1$H-NMR δ (DMSO-$d_6$) 0.95 (3H, t, J=6.0 Hz), 1.20 (9H, s), 4.29 (1H, d, J=11.7 Hz), 4.49–4.55 (3H, m), 4.61 (1H, m), 5.11 (2H, s).

In the same manner as in Example 7 (b), the title compound is obtained from the above compound.

$^1$H-NMR δ (DMSO-$d_6$) 0.96 (3H, t, J=7.1 Hz), 1.18 (9H, s), 4.36 (2H, d, J=5.7 Hz), 5.11 (2H, s), 8.07(1H, s). Hydrochloride: mp 149–150° C.

Example 50

Preparation of N-[1-butyl-4-[3-(3-pyridylmethoxy)phenyl]-1,2-dihydro-2-oxo-1,8-naphthyridin-3-yl]-N'-[2,6-diisbpropyl-4-(hydroxymethyl)phenyl]urea:

In the same manner as in Example 24 (a), N-[1-butyl-4-[3-(3-pyridylmethoxy)phenyl]-1,2-dihydro-2-oxo-1,8-naphthyridin-3-yl]-N'-[2,6-diisopropyl-4-(tert-butyldimethylsilyloxymethyl)phenyl]urea is obtained from 3-amino-1-butyl-4-[3-(3-pyridylmethoxy)phenyl]-1,2-dihydro-2-oxo-1,8-naphthyridine and 2,6-diisopropyl-4-(tert-butyl-dimethylsilyloxymethyl)aniline.

$^1$H-NMR δ (DMSO-$d_6$) 0.02 (6H, s), 0.84 (9H, s), 0.89–0.94 (15H, m), 4.47 (2H, t, J=6.8 Hz), 4.58 (2H, s), 5.09 (2H, s).

In the same manner as in Example 41 (b), the title compound is obtained from the above compound.

$^1$H-NMR δ (DMSO-d6) 0.94–1.01 (15H, m), 4.40 (2H, d, J=5.7 Hz), 4.51 (2H, t, J=7.1 Hz), 5.05 (1H, t, J=5.7 Hz), 5.14 (2H, s), 7.59 (1H, s). Hydrochloride: mp 170–171° C.

Example 51

Preparation of N-[1-butyl-4-[3-[3-(hydroxy)propoxy]phenyl]-1,2-dihydro-2-oxo-1,8-naphthyridin-3-yl]-N'-[2-tert-butyl-5-(1-pyrazolylmethyl)-phenyl]urea:
(a) Preparation of N-[1-butyl-4-[3-[3-(benzyloxy)propoxy]phenyl]-1,2-dihydro-2-oxo-1,8-naphthyridin-3-yl]-N'-[2-tert-butyl-5-(1-pyrazolylmethyl)phenyl]urea:

In the same manner as in Example 24 (a), the title compound is obtained from 3-amino-1-butyl-4-[3-[3-(benzyloxy)propoxy]phenyl]-1,2-dihydro-2-oxo-1,8-naphthyridine and 2-tert-butyl-5-(1-pyrazolylmethyl) aniline.

$^1$H-NMR δ (DMSO-$d_6$) 0.98 (3H, t, J=7.3 Hz), 1.17 (9H, s), 3.55 (2H, t, J=6.3 Hz), 4.03 (2H, t, J=6.3 Hz), 4.40 (2H, s), 5.18 (2H, s), 6.22 (1H, br s), 8.07 (1H, br s).

(b) Preparation of N-[1-butyl-4-[3-[3-(hydroxy)propoxy]phenyl]-1,2-dihydro-2-oxo-1,8-naphthyridin-3-yl]-N'-[2-tert-butyl-5-(1-pyrazolylmethyl) phenyl]urea:

A suspension of N-[1-butyl-4-[3-[3-(benzyloxy)propoxy]phenyl]-1,2-dihydro-2-oxo-1,8-naphthyridin-3-yl]-N'-[2-tert-butyl-5-(1-pyrazolylmethyl)phenyl]urea (1.86 g, 2.6 mmol), 10% palladium carbon (180 mg), conc. hydrochloric acid (0.21 ml, 2.6 mmol) in methanol is stirred under hydrogen atmosphere at room temperature for 8 hours. The mixture is filtered on celite, and the solvent is concentrated under reduced pressure. The resultant is dissolved in chloroform, and thereto are added water and aqueous ammonia. The mixture is stirred and the chloroform layer is dried over anhydrous sodium sulfate, and the solvent is concentrated under reduced pressure. The residue is purified by silica gel column chromatography to give the title compound (1.53 g, 2.46 mmol) as colorless amorphous.

$^1$H-NMR δ (DMSO-$d_6$) 0.98 (3H, t, J=7.3 Hz), 1.19 (9H, s), 4.01 (2H, t, J=6.3 Hz), 4.52 (3H, br), 5.20 (2H, s), 6.23 (1H, s), 8.06 (1H, s). Hydrochloride: mp 116–119° C.

Example 52

Preparation of N-[1-butyl-4-(3-hydroxyphenyl)-1,2-dihydro-2-oxo-1,8-naphthyridin-3-yl]-N'-[2-tert-butyl-5-(1-imidazolylmethyl)phenyl]urea:

To a solution of N-[1-butyl-4-(3-methoxyphenyl)-1,2-dihydro-2-oxo-1,8-naphthyridin-3-yl]-N'-[2-tert-butyl-5-(1-imidazolylmethyl)phenyl]-urea (3.79 g, 6.16 mmol) in methylene chloride (50 ml) is added dropwise a solution of boron tribromide (6.18 g, 24.64 mmol) in methylene chloride under ice-cooling. After the addition, the mixture is stirred at room temperature for 3 hours. To the mixture are added successively water, an aqueous sodium hydrogen carbonate solution, ethyl acetate, and a 2N aqueous sodium hydroxide solution, and the mixture is stirred. The mixture is separated, and the organic layer is concentrated under reduced pressure. The precipitated crystals are collected by filtration, and suspended in acetonitrile. The mixture is stirred for 2 hours, and the precipitates are collected by filtration to give the title compound (3.24 g, 5.74 mmol) as colorless crystals.

$^1$H-NMR δ (DMSO-$d_6$) 0.96 (3H, t, J=7.3 Hz), 1.20 (9H, s), 4.50 (2H, t, J=7.3 Hz), 5.05 (2H, s), 6.23 (1H, m), 8.09 (1H, br s). Hydrochloride: mp 160–162.5° C.

Examples 53–55

In the same manner as in Example 25, the compounds as listed in Table 4 are obtained from N-[1-butyl-4-(3-hydroxyphenyl)-1,2-dihydro-2-oxo-1,8-naphthyridin-3-yl]-N'-[2-tert-butyl-5-(1-imidazolylmethyl)phenyl]urea.

TABLE 4

[Structure: 4-(3-OR²⁴-phenyl)-1-butyl-1,2-dihydro-2-oxo-1,8-naphthyridin-3-yl urea linked to 2-tert-butyl-5-(1-imidazolylmethyl)phenyl]

| Ex. No. | R²⁴ | Physicochemical properties |
|---|---|---|
| 53 | —(CH₂)₂NEt₂ | Hydrochloride: mp 136–142° C. |
| 54 | —(CH₂)₃OBn | ¹H-NMR δ(DMSO-d₆) 0.98 (3H, t, J=7.3Hz), 1.20(9H, s), 3.55(2H, t, J=6.2Hz), 4.02(2H, t, J=6.2Hz), 4.44 (2H, s), 4.50(2H, br), 5.05 (2H, s), 8.11(1H, br s). |
| 55 | —(CH₂)₄-(1-piperidinyl) | Hydrochloride: mp 148–151.5° C. |

Bn means a benzyl group.

Example 56
Preparation of N-[-butyl-4-[3-[3-(hydroxy)propoxy]phenyl]-1,2-dihydro-2-oxo-1,8-naphthyridin-3-yl]-N'-[2-tert-butyl-5-(1-imidazolylmethyl)-phenyl]urea:

In the same manner as in Example 51 (b), the title compound is obtained from N-[1-butyl-4-[3-[3-(benzyloxy)propoxy]phenyl]-1,2-dihydro-2-oxo-1,8-naphthyridin-3-yl]-N'-[2-tert-butyl-5-(1-imidazolylmethyl)phenyl]urea.

¹H-NMR δ (DMSO-d₆) 0.98 (3H, t, J=7.3 Hz), 1.19 (9H, s), 4.00 (2H, t, J=6.3 Hz), 5.06 (2H, s), 8.10 (1H, br s). Hydrochloride: mp 126–134° C.

Example 57
Preparation of N-[1-butyl-4-(3-methoxyphenyl)-1,2-dihydro-2-oxo-1,8-naphthyridin-3-yl]-N'-(2,6-diisopropyl-4-aminophenyl)urea:

(a) Preparation of N-[1-butyl-4-(3-methoxyphenyl)-1,2-dihydro-2-oxo-1,8-naphthyridin-3-yl]-N'-(2,6-diisopropyl-4-tritylaminophenyl)urea:

In the same manner as in Example 24 (a), the title compound is obtained from 3-amino-1-butyl-4-(3-methoxyphenyl)-1,2-dihydro-2-oxo-1,8-naphthyridine and 2,6-diisopropyl-4-tritylaminoaniline.

¹H-NMR δ (DMSO-d₆) 0.70–0.76 (12H, br), 0.96 (3H, t, J=7.1 Hz), 4.49 (2H, t, J=7.7 Hz), 7.14–7.37 (17H, m), 8.56 (1H, dd, J=4.6 Hz, 1.7 Hz).

(b) Preparation of N-[1-butyl-4-(3-methoxyphenyl)-1,2-dihydro-2-oxo-1,8-naphthyridin-3-yl]-N'-(2,6-diisopropyl-4-aminophenyl)urea:

A suspension of N-[1-butyl-4-(3-methoxyphenyl)-1,2-dihydro-2-oxo-1,8-naphthyridin-3-yl]-N'-(2,6-diisopropyl-4-tritylaminophenyl)urea (273 mg, 0.348 mmol), a 10% palladium carbon (56 mg) in ethanol is stirred under hydrogen atmosphere at room temperature for 8 hours. The mixture is filtered on celite, and the solvent is concentrated under reduced pressure. The residue is purified by silica gel column chromatography to give the title compound (165 mg, 0.30 mmol) as crystals.

¹H-NMR δ (DMSO-d₆) 0.91–0.99 (15H, m), 3.76 (2H, s), 4.51 (2H, t, J=7.7 Hz), 6.23 (2H, s), 7.22 (1H, dd, J=7.9 Hz, 4.8 Hz).

Example 58
Preparation of N-[1-butyl-4-(3-methoxyphenyl)-1,2-dihydro-2-oxo-1,8-naphthyridin-3-yl]-N'-[2,6-diisopropyl-4-(3-pyridylmethylamino)phenyl]-urea:

To a solution of N-[1-butyl-4-(3-methoxyphenyl)-1,2-dihydro-2-oxo-1,8-naphthyridin-3-yl]-N'-(2,6-diisopropyl-4-aminophenyl)urea (450 mg, 0.727 mmol) in methanol (5 ml) are added nicotinaldehyde (0.137 ml, 1.45 mmol) and conc. hydrochloric acid (0.12 ml, 1.44 mmol) at room temperature. Then, the mixture is cooled under ice-cooling, and thereto is added sodium borohydride (68.6 mg, 1.09 ml), and the mixture is stirred at room temperature for 5 hours. To the mixture is added water, and the mixture is extracted with ethyl acetate. The organic layer is washed twice with an aqueous sodium hydrogen carbonate solution and then dried over anhydrous magnesium sulfate. The solvent is concentrated under reduced pressure, and the residue is purified by silica gel column chromatography to give the title compound (475 mg, 0.654 mmol) as colorless amorphous.

¹H-NMR δ (DMSO-d₆) 0.88–1.03 (15H, m), 3.75 (3H, s), 4.23 (2H, d, J=5.7 Hz), 4.51 (2H, t, J=7.5 Hz), 7.65 (1H, s), 8.55 (1H, s). Hydrochloride: mp 160–161° C.

Example 59
Preparation of N-[1-butyl-4-(3-methoxyphenyl)-1,2-dihydro-2-oxo-1,8-naphthyridin-3-yl]-N'-[2,6-diisopropyl-4-[N-(3-pyridylmethyl)-N-methylamino]phenyl]urea:

To a solution of N-[1-butyl-4-(3-methoxyphenyl)-1,2-dihydro-2-oxo-1,8-naphthyridin-3-yl]-N'-[2,6-diisopropyl-4-(3-pyridylmethylamino)-phenyl]urea (476 mg, 0.752 mmol) in methanol (5 ml) are added a 37% aqueous formaldehyde solution (122 mg, 1.50 ml) and conc. hydrochloric acid (0.13 ml, 1.50 ml) at room temperature. The mixture is cooled with ice, and the thereto is added sodium cyanoborohydride (71.0 mg, 1.13 ml), and the mixture is stirred at room temperature for 5 hours. To the mixture is added water, and the mixture is extracted with ethyl acetate. The organic layer is extracted twice with sodium hydrogen carbonate, and dried over anhydrous magnesium sulfate. The solvent is concentrated under reduced pressure, and the residue is purified by silica gel column chromatography to give the title compound (445 mg, 0.684 mmol) as colorless amorphous.

¹H-NMR δ (DMSO-d₆) 0.94–0.97 (15H, m), 2.99 (3H, s), 3.76 (3H, s), 4.49–4.52 (4H, m), 6.35 (2H, s), 8.41 (2H, m), 8.46 (1H, s). Hydrochloride: mp 155–157° C.

Example 60
Preparation of N-[1-butyl-4-[3-[3-(hydroxy)propoxy]phenyl]-1,2-dihydro-2-oxo-1,8-naphthyridin-3-yl]-N'-[2,6-diisopropyl-4-aminophenyl]urea:

(a) Preparation of N-1-butyl-4-[3-[3-(benzyloxy)propoxy]phenyl]-1,2-dihydro-2-oxo-1,8-naphthyridin-3-yl]-N'-[2,6-diisopropyl-4-tritylaminophenyl]urea:

In the same manner as in Example 24 (a), the title compound is obtained from 3-amino-1-butyl-4-[3-[3-(benzyloxy)propoxy]phenyl]-1,2-dihydro-2-oxo-1,8-naphthy and 2,6-diisopropyl-3-tritylaminoaniline.

¹H-NMR δ (DMSO-d₆) 0.81 (3H, d, J=6.8 Hz), 0.88 (3H, d, J=6.8 Hz), 0.97 (3H, t, J=7.3 Hz), 3.58 (2H, t, J=6.2 Hz), 4.05 (2H, t, J=6.2 Hz), 4.51 (2H, t, J=7.0 Hz), 5.18 (1H, s), 5.85 (1H, d, J=8.6 Hz), 7.51 (1H, s), 7.73 (1H, s).

(b) Preparation of N-[1-butyl-4-[3-[3-(benzyloxy)propoxy]phenyl]-1,2-dihydro-2-oxo-1,8-naphthyridin-3-yl]-N'-[2,6-diisopropyl-4-aminophenyl]urea:

To a solution of N-[1-butyl-4-[3-[3-(benzyloxy)propoxy]phenyl]-1,2-dihydro-2-oxo-1,8-naphthyridin-3-yl]-N'-[2,6-diisopropyl-4-tritylaminophenyl]urea (1.60 g, 1.74 mmol) in a mixture of acetone (20 ml) and methanol (20 ml) is added conc. hydrochloric acid (1 ml, 12 mmol) under ice-cooling, and the mixture is stirred at room temperature for 14 hours. The reaction solution is made basic by adding thereto aqueous ammonia under ice-cooling, and extracted with ethyl acetate. The organic layer is washed twice with aqueous sodium hydrogen carbonate solution, and the solvent is concentrated under reduced pressure. The residue is purified by silica gel column chromatography to give the title compound (1.07 g, 1.58 mmol).

$^1$H-NMR δ (DMSO-$d_6$) 0.89–1.20 (17H, m), 3.58 (2H, t, J=6.2 Hz), 4.05 (2H, t, J=6.4 hz), 7.53 (1H, s), 7.67 (1H, s). Hydrochloride: mp 136–139° C.

(c) Preparation of N-[1-butyl-4-[3-[3-(hydroxy)propoxy]phenyl]-1,2-dihydro-2-oxo-1,8-naphthyridin-3-yl]-N'-[2,6-diisopropyl-4-aminophenyl]urea:

In the same manner as in Example 51 (b), the title compound is obtained.

$^1$H-NMR δ (DMSO-$d_6$) 0.90–1.20 (15H, m), 3.52–3.58 (2H, m), 3.99–4.06 (2H, m), 4.41 (2H, br), 4.52 (2H, t, J=7.3 Hz), 7.53 (1H, s), 7.68 (1H, s), Hydrochloride: mp 153–155° C.

Examples 61–64

The compounds as listed in Table 5 are obtained in the same manner as in Example 60 (a) and (b).

TABLE 5

| Ex. No. | $R^{24}$ | Physiochemical properties |
|---|---|---|
| 61 | propyl-piperidinyl | Hydrochloride: mp 185–187° C. |
| 62 | butyl-piperidinyl | Hydrochloride: mp 176–177° C. |
| 63 | ethyl-pyridyl | Hydrochloride: mp 175–176° C. |
| 64 | —(CH$_2$)$_2$NEt$_2$ | Hydrochloride: mp 175–176° C. |

Example 65
Preparation of N-[1-butyl-4-[3-[3-(hydroxy)propoxy]phenyl]-1,2-dihydro-2-oxo-1,8-naphthyridin-3-yl]-N'-(2,6-diisopropyl-4-aminophenyl)urea:

In the same manner as in Example 24 (a), N-[1-butyl-4-[3-[3-(benzyloxy)propoxy]phenyl]-1,2-dihydro-2-oxo-1,8-naphthyridin-3-yl]N'-(2,6-diisopropyl-4-tritylaminophenyl)urea is obtained from 3-amino-1-butyl-4-3-[3-(benzyloxy)propoxy]phenyl]-1,2-dihydro-2-oxo-1,8-naphtyridine and 2,6-diisopropyl-4-tritylaminoaniline.

$^1$H-NMR δ (DMSO-$d_6$) 0.70–0.81 (12H, m), 0.95 (3H, t, J=7.1 Hz), 3.58 (2H, t, J=6.2 Hz), 4.02 (2H, m), 4.46–4.49 (2H, m), 6.15 (1H, s), 6.51 (1H,

A suspension of the above compound (1.93 g, 2.10 mmol), conc. hydrochloric acid (0.190 ml, 2.31 mmol) and a 10% palladium carbon (580 mg) in methanol (50 ml) is stirred at room temperature under hydrogen atmosphere for 8 hours. The mixture is filtered on celite, and the solvent is concentrated under reduced pressure. The resultant is extracted with ethyl acetate, and the organic layer is washed twice with an aqueous sodium hydrogen carbonate solution, and dried over anhydrous magnesium sulfate. The solvent is concentrated under reduced pressure, and the residue is purified by silica gel column chromatography to give the title compound (834 mg, 1.43 mmol) as colorless amorphous.

$^1$H-NMR δ (DMSO-$d_6$) 0.92–1.00 (15H, m), 3.52–3.58 (2H, m), 3.99–4.06 (2H, m), 4.52–4.54 (3H, m), 4.80 (2H, br), 6.23 (2H, s), 7.64 (1H, s). Hydrochloride: mp 175–176° C.

Example 66

Preparation of N-[1-butyl-4-(3-methoxyphenyl)-1,2-dihydro-2-oxo-1,8-naphthyridin-3-yl]-N'-[2,6-diisopropyl-3-(3-pyridylmethylamino)phenyl]-urea:

In the same manner as in Example 58, the title compound is obtained from N-[1-butyl-4-(3-methoxyphenyl)-1,2-dihydro-2-oxo-1,8-naphthyridin-3-yl]-N'-(2,6-diisopropyl-3-aminophenyl)urea.

$^1$H-NMR δ (DMSO-$d_6$) 0.88–1.22 (15H, m), 3.27–3.36 (2H, m), 3.77 (3H, s), 4.52 (2H, t, J=8.2 Hz), 6.28 (1H, d, J=8.6 Hz), 6.73 (1H, d, J=8.6 hz).

Example 67

Preparation of N-[1-butyl-4-(3-methoxyphenyl)-1,2-dihydro-2-oxo-1,8-naphthyridin-3-yl]-N'-[2,6-diisopropyl-3-(3-pyridylcarbonylamino)-phenyl]urea:

A solution of N-[1-butyl-4-(3-methoxyphenyl)-1,2-dihydro-2-oxo-1,8-naphthyridin-3-yl]-N'-(2,6-diisopropyl-3-aminophenyl)urea (300 mg, 0.485 mmol), nicotinic acid (66 mg, 0.533 mmol), 1-hydroxybenzotriazole (131 mg, 0.97 mmol), 1-ethyl-3-(3'-dimethylaminopropyl)carbodiimide hydrochloride (93 mg, 0.485 mmol) and Et$_3$N (0.06 ml, 0.485 mmol) in DMF (10 ml) is stirred at room temperature overnight. To the reaction solution is added water, and the mixture is extracted with ethyl acetate. The organic layer is washed twice with an aqueous ammonium chloride solution, and washed twice with an aqueous sodium hydrogen carbonate solution. The solvent is concentrated under reduced pressure, and the residue is purified by silica gel column chromatography to give the title compound (243 mg, 0.373 mmol) as white crystals.

$^1$H-NMR δ (DMSO-$d_6$) 0.95–1.20 (15H, m), 3.77 (3H, s), 4.52 (2H, t, J=7.3 Hz), 6.91–7.12 (5H, m), 7.75 (2H, s), 9.92 (1H, s). Hydrochloride: mp 179–180° C.

Examples 68–73

The compounds as listed in Table 6 are obtained in the same manner as in Example 67.

TABLE 6

[Structure: 4-(3-methoxyphenyl)-1-butyl-1,2-dihydro-2-oxo-1,8-naphthyridin-3-yl urea linked to 2-tert-butyl-5-(NHC(O)R²⁶)phenyl]

| Ex. No. | R²⁶ | Physiochemical properties |
|---|---|---|
| 68 | 2-pyridyl | Hydrochloride: mp 145–146° C. |
| 69 | 4-pyridyl | ¹H-NMR δ(DMSO-d₆) 0.94–1.15 (15H, m), 3.77(3H, s), 4.52(2H, m), 6.90(2H, m), 7.75(1H, s), 7.85(2H, d, J=6.0Hz), 8.80(2H, d, J=6.0Hz), 10.00(1H, s). |
| 70 | —CH₂NMe₂ | Hydrochloride: mp 162–163° C. |
| 71 | —CH₂NEt₂ | hydrochloride: mp 159–160° C. |
| 72 | 3-pyridylmethyl | Hydrochloride: mp 175–176° C. |
| 73 | 1-piperidinylethyl | Hydrochloride: mp 164–166° C. |

Example 74

Preparation of N-[1-butyl-4-(3-methoxyphenyl)-1,2-dihydro-2-oxo-1,8-naphthyridin-3-yl]-N'-[2-tert-butyl-[5-(3-pyridyl)aminocarbonyl]phenyl]-urea:

(a) Preparation of N-[1-butyl-4-(3-methoxyphenyl)-1,2-dihydro-2-oxo-1,8-naphthyridin-3-yl]-N'-[2-tert-butyl-(5-methoxycarbonyl)phenyl]urea:

In the same manner as in Example 1, the title compound is obtained from 1-butyl-3-carboxy-4-(3-methoxyphenyl)-1,2-dihydro-2-oxo-1,8-naphthyridine and 2-tert-butyl-(5-methoxycarbonyl)aniline.

¹H-NMR δ (DMSO-d₆) 0.96 (3H, t, J=7.3 Hz), 1.23 (9H, s), 3.73 (3H, s), 3.81 (3H, s), 6.89 (1H, s), 7.73 (1H, s), 8.17 (1H, s).

(b) Preparation of N-[1-butyl-4-(3-methoxyphenyl)-1,2-dihydro-2-oxo-1,8-naphthyridin-3-yl]-N'-[2-tert-butyl-(5-carboxy)phenyl]urea:

To a suspension of N-[1-butyl-4-(3-methoxyphenyl)-1,2-dihydro-2-oxo-1,8-naphthyridin-3-yl]-N'-[2-tert-butyl-(5-methoxycarbonyl)phenyl]urea (17.1 g, 30.7 mmol) in ethanol (500 ml) is added a 10N aqueous sodium hydroxide solution (10 ml, 92.2 mmol), and the mixture is heated with stirring at about 50° C. for 3 hours. The reaction solution is made acidic with a 3N aqueous hydrochloric acid solution, and the resulting colorless crystals are collected by filtration, and washed with hexane, and dried to give the title compound (14.9 g, 27.4 mmol).

¹H-NMR δ (DMSO-d₆) 0.98 (3H, t, J=7.3 Hz), 1.24 (9H, s), 3.74 (3H, s), 6.89 (1H, s), 7.74 (1H, s), 8.14 (1H, s).

(c) Preparation of N-[1-butyl-4-(3-methoxyphenyl)-1,2-dihydro-2-oxo-1,8-naphthyridin-3-yl]-N'-[2-tert-butyl-[5-(3-pyridyl)aminocarbonyl]phenyl]urea:

To a suspension of N-[1-butyl-4-(3-methoxyphenyl)-1,2-dihydro-2-oxo-1,8-naphthyridin-3-yl]-N'-[2-tert-buthyl-(5-carboxy)phenyl]urea (500mg, 0.90 mmol) in dimethylformamide (30 ml) are added isobutyl chlorocarbonate (0.12 ml, 0.90 mmol) and triethylamine (0.13 ml, 0.90 mmol), and the mixture is stirred at room temperature for two hours. To the mixture is added 3-aminopyridine (70 mg, 0.90 mmol), and the mixture is stirred at room temperature for 14 hours. To the reaction solution are added water, a saturated birine and ethyl acetate, and the mixture is separated. The organic layer is washed successively with water and a saturated brine, and dried over anhydrous magnesium sulfate. The solvent is evaporated under reduced pressure, and the residue is purified by silica gel column chromatography, and crytalized from ethyl acetate/hexane to give the title compound (93.3 mg, 0.15 mmol) as colorless crystals.

¹H-NMR δ (DMSO-d₆) 0.96 (3H, t, J=7.3 Hz), 1.24 (9H, s), 1.41 (2H, m), 1.70 (2H, m), 3.71 (3H, s), 10.35 (1H, s). Hydrochloride: mp 178–180° C.

Examples 75–78

The compounds as listed in Table 7 are obtained in the same manner as in Example 74.

TABLE 7

[Structure: 4-(3-methoxyphenyl)-1-butyl-1,2-dihydro-2-oxo-1,8-naphthyridin-3-yl urea linked to 2-tert-butyl-5-(C(O)NH-R²⁷)phenyl]

| Ex. No. | R²⁷ | Physiochemical properties |
|---|---|---|
| 75 | 3-pyridylmethyl | mp 140–143° C. |
| 76 | 4-pyridyl | mp 190–195° C. |
| 77 | —(CH₂)₂NEt₂ | mp 133–135° C. |
| 78 | 1-piperidinylpropyl | mp 128–130° C. |

Example 79

Preparation of N-[1-butyl-4-[3-(3-piperidinopropoxy)phenyl]-1,2-dihydro-2-oxo-1,8-naphthyridin-3-yl]-N'-(2,6-diisopropyl-4-hydroxyphenyl)urea:

In the same manner as in Example 24, the title compound is obtained from 1-butyl-3-amino-4-[3-(3-piperidinopropoxy)phenyl]-1,2-dihydro-2-oxo-1,8-naphthyridine.

$^1$H-NMR δ (DMSO-d$_6$) 0.93–1.44 (17H, m), 4.00 (2H, m), 4.50 (2H, t, J=7.7 Hz), 6.40 (2H, s), 6.85–6.88 (2H, m), 7.49 (1H, s), 7.60 (1H, dd, J=8.1 Hz, 1.7 Hz), 7.68 (1H, s), 8.59 (1H, dd, J=4.6 Hz, 1.7 Hz), 8.05 (1H, s).

Example 80
Preparation of N-[1-butyl-4-[3-(3-piperidinopropoxy)phenyl]-1,2-dihydro-2-oxo-1,8-naphthyridin-3-yl]-N'-(2,6-diisopropyl-3-hydroxyphenyl)urea:

N-1-Butyl-4-[3-(3-piperidinopropoxy)phenyl]-1,2-dihydro-2-oxo-1,8-naphthyridin-3-yl]-N'-(2,6-diisopropyl-3-aminophenyl)urea (100 mg, 0.138 mmol) is dissolved in a 12% aqueous hydrogen bromide solution at room temperature, and thereto is added an aqueous solution (1 ml) of sodium nitrite (13 mg, 0.152 mmol) under ice-cooling. The mixture is stirred under ice-cooling for 30 minutes and then, the reaction mixture is added an aqueous solution (1 ml) of potassium cyanide (33.7 mg, 0.58 mmol) and cuprous cyanide (15.5 mg, 0.173 mmol). The mixture is warmed to about 70° C., and the mixture is stirred for 5 hours. The mixture is extracted with ethyl acetate, and the organic layer is washed twice with an aqueous sodium hydrogen carbonate solution, and dried over anhydrous magnesium sulfate. The solvent is concentrated under reduced pressure, and the residue is purified by silica gel column chromatography to give the title compound (36 mg, 0.055 mmol) as colorless amorphous.

$^1$H-NMR δ (DMSO-d$_6$) 0.98–1.52 (21H, m), 4.03–4.13 (2H, m), 4.58 (2H, t, J=7.3 Hz), 6.67 (1H, d, J=8.4 Hz), 6.86 (1H, d, J=8.6 Hz), 6.94–6.97 (2H, m), 7.03–7.06 (1H, m), 7.30 (1H, dd, J=8.0 Hz, 4.6 Hz), 7.70(1H, s), 7.75 (1H, s), 8.94 (1H, s).

Reference Example 1
Preparation of 2,6-diisopropyl-4-(3-chllrobenzoyloxy) aniline:

To a solution of m-chloroperbenzoic acid (20.0 g, 100 mmol) in methylene chloride (200 ml) is added dropwise a solution of 2,6-diisopropylaniline (10.0 g, 56.4 mmol) in methylene chloride (30 ml) under ice-cooling, and the mixture is stirred at the same temperature for one hours and then stirred at room temperature for 12 hours. To the mixture is added an aqueous sodium thiosulfate solution, and the mixture is stirred for 0.5 hour, and then extracted with ethyl acetate. The extract is washed with an aqueous sodium thiosulfate solution (twice), an aqueous sodium hydrogen carbonate solution (twice), and a saturated brine (once), and dried over anhydrous magnesium sulfate, and concentrated under reduced pressure. The resulting residue is purified by silica gel column chromatography (ethyl acetate:hexane= 1:20→ethyl acetate:hexane=1:10) to give the title compound (4.0 g, 12.0 mmol) as oil.

$^1$H-NMR δ (CDCl$_3$)1.28 (12H, d, J=6.8 Hz), 2.95 (2H, sep, J=6.8 Hz), 6.86 (2H, s), 7.44 (1H, dd, J=9.0 Hz, 7.7 Hz), 7.59 (1H, d, J=9.0 Hz), 8.09 (1H, d, J=7.7 Hz), 8.19 (1H, t, J=1.7 Hz).

Experiment
The ACAT inhibitory activity of the present compounds is evaluated by the following method.
1. Assay of ACAT inhibitory activity in a specimen prepared from rabbit liver:

An enzyme specimen ACAT was prepared according to the method disclosed in the literature: J. Lipid. Research, 30, 681–690, 1989, from the liver of a New Zealand white rabbit, which had been fed with 1% cholesterol feed for one month. The ACAT activity was determined according to the method disclosed in the literature: J. Lipid Research, 24, 1127–1134, 1983, i.e., using radioactive [1-$^{14}$C]oleoyl-CoA and endogenous cholesterol contained in the liver microsome, and calculated from the radioactivity of the labeled cholesterol oleate. The results are shown in Table 8.

TABLE

| Test compound (Example No.) | ACAT inhibitory rate (%) $10^{-6}$ M |
| --- | --- |
| 1 | 98 |
| 19 | 99 |

2. Assay of ACAT inhibitory activity in a macrophage derived from rat peritoneal:

The rat peritoneal-derived macrophage was prepared according to the method disclosed in the literature: Biochimica et Biophysica Acta, 1126, 73–80, 1992. The ACAT activity was determined by a modified method of the method disclosed in the above literature: Biochimica et Biophysica Acta, 1126, 73–80, 1992, i.e., using radioactive [9,10-$^3$H] oleic acid and exogenous cholesterol contained in the liposome which was re-constituted according to the method disclosed in the literature: Biochimica et Biophysica Acta, 1213, 127–134, 1994, and calculated from the radioactivity of the labeled cholesterolyl oleate. The results are shown in Table 9.

TABLE 9

| Test compound (Example No.) | ACAT inhibitory rate (%) $10^{-6}$ M |
| --- | --- |
| 1 | 97 |
| 19 | 73 |

INDUSTRIAL APPLICABILITY

The compound of the present invention strongly inhibits ACAT activity in a specimen prepared from rabbit liver or in rat peritoneal-derived macrophage. Therefore, the present compound is useful not only as an agent for treatment of hyperlipidemia, but also in the prophylaxis or treatment of atherosclerosis per se or various diseases accompanied by atherosclerosis, for example, cerebral infarction, cerebral thrombosis, transient cerebral ischemia, angina pectoris, myocardial infarction, peripheral thrombus or occlusion.

What is claimed is:
1. A compound of the formula (1):

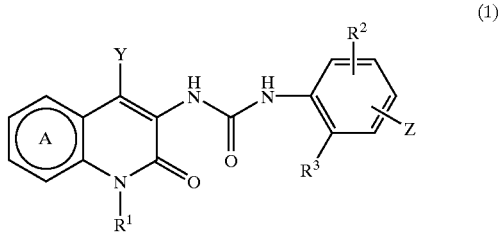

(1)

wherein Ring A is a substituted or unsubstituted pyridine ring, wherein the pyridine ring is one of the groups of the following formulae (a), (b) and (c)

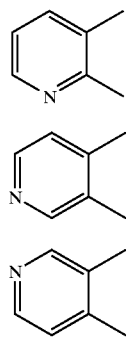

Y is a substituted or unsubstituted aromatic group,
R¹ is a hydrogen atom, a substituted or unsubstituted alkyl group, or a substituted or unsubstituted alkenfyl group,
R² is a hydrogen atom or a lower alkyl group,
R³ is a lower alkyl group,
Z is a hydroxyl group, or a group of the formula: —NR⁴R⁵ (R⁴ and R⁵ are independently a hydrogen atom, a lower alkoxy-substituted lower alkyl group, a cycloalkyl group, or an aralkyl group, or R⁴ and R⁵ may combine each other, and with the adjacent nitrogen atom to which they bond, form a saturated cyclic amino group having 4 to 8 carbon atoms as ones forming said ring, and optionally having one —NR⁸— (R⁸ is a hydrogen atom, a substituted or unsubstituted lower alkyl group, a substituted or unsubstituted phenyl group, a substituted or unsubstituted benzyl group, or a lower alkoxycarbonyl group) or one oxygen atom in the cycle thereof), or a prodrug thereof, or a pharmaceutically acceptable salt of the same.

2. The compound according to claim 1, or a prodrug thereof, or a pharmaceutically acceptable salt of the same, wherein Y is a phenyl group being substituted by a group of the formula: —M¹—E¹—T (M¹ is a direct bond, an oxygen atom, a sulfur atom, or a group of the formula: —NR⁶¹— (R⁶¹ is a hydrogen atom or a lower alkyl group), E¹ is a divalent hydrocarbon group having 1 to 8 carbon atoms and optionally containing an unsaturated bond, and T is a hydroxy group, a halogen atom, a carboxyl group, a lower alkoxycarbonyl group, a benzyloxycarbonyl group, a cyano group, a benzyloxy group, a lower alkoxy group, a lower alkanoyloxy group, a lower alkylthio group, a lower alkylsulfinyl group, a lower alkylsulfonyl group, a methanesulfonyloxy group, an alkyl-substituted or unsubstituted benzenesulfonyloxy group, a lower aikanoylamino group, a lower alkoxycarbonylamino group, a lower alkylsulfonamido group, a phthalimido group, a substituted or unsunstituted heteroaryl group, or a group of the formula: —NR⁴¹R⁵¹ (R⁴¹ and R⁵¹ are independently a hydrogen atom, a lower alkoxy-substituted or unsubstituted lower alkyl group, a cycloalkyl group, a lower alkoxycarbonyl group, or an aralkyl group, or R⁴¹ and R⁵¹ may combine each other, and with the adjacent nitrogen atom to which they bond, form a saturated cyclic amino group having 4 to 8 carbon atoms as ones forming the said ring, and optionally having one —NR⁸¹— (R⁸¹ is a hydrogen atom, a substituted or unsubstituted lower alkyl group, a substituted or unsubstituted phenyl group, a substituted or unsubstituted benzyl group, or a lower alkoxycarbonyl group) or one oxygen atom in the cycle thereof), or a group of the formula: —C(=O)NR⁴¹R⁵¹ (R⁴¹ and R⁵¹ are as defined above)).

3. The compound according to claim 2, or a prodrug thereof, or a pharmaceutically acceptable salt of the same, wherein M¹ is an oxygen atom, E¹ is a hydrocarbon group having 2 to 4 carbon atoms, and T is a hydroxygroup or a group of the formula:—NR⁴¹R⁵¹.

4. The compound according to claim 3, or a prodrug thereof, or a pharmaceutically acceptable salt of the same, which is a compound of the formula (51):

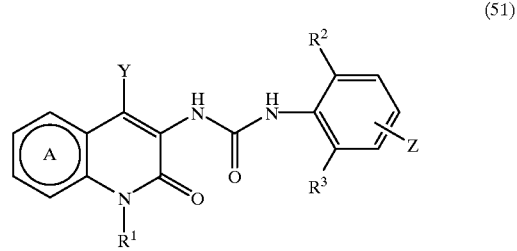

(51)

wherein Ring A, Y, R¹, R², R³ and Z are as defined below:
wherein Ring A is a substituted or unsubstituted pyridine ring,
wherein the pyridine ring is one of the groups of the following formulae (a), (b) and (c):

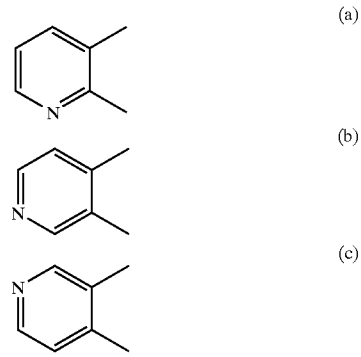

Y is a substituted or unsubstituted aromatic group,
R¹ is a hydrogen atom, a substituted or unsubstituted alkyl group, or a substituted or sunsubstituted alkenyl group,
R² is a hydrogen atom or a lower alykl group,
R³ is a lower alkyl group,
Z is a hydroxyl group, or a group of the formula: -NR⁴R⁵ (R⁴ and R⁵ are independently a hydrogen atom, a lower alkoxy-substituted lower alkyl group, a cycloalkyl group, or an aralkyl group, or R⁴ and R⁵ may combine each other, and with the adjacent nitrogen atom to which they bond, form a saturated cyclic amino group having 4 to 8 carbon atoms as ones forming said ring, and optionally having one -NR⁸— (R⁸ is a hydrogen atom, a substituted or unsubstituted lower alkyl group, a substituted or unsubstituted phenyl group, a substituted or unsubstituted benzyl group, or a lower alkoxycarbonyl group) or one oxygen atom in the cycle thereof), or a prodrug thereof, or a pharmaceutically acceptable salt of the same.

5. The compound according to claim 1, which is N-[1-butyl-4-(3-(3-hydroxypropoxy)phenyl)-1,2-dihydro-2-oxo-1,8-naphthyridin-3-yl]-N'-(2,6-diisopropyl-4-aminophenyl) urea, or a prodrug thereof, or a pharmaceutically acceptable salt of the same.

6. A pharmaceutical composition comprising the compound as set forth in any one of claims 1, 2, 3, 4, or 5, or a prodrug thereof, or a pharmaceutically acceptable salt of the same.

7. A method for inhibiting acyl-CoA: cholesterol acyl transferase (ACAT) in a patient in need, which comprises administering a therapeutically effective amount of the compound as set forth in any one of claims 1, 2, 3, 4, or 5, or a prodrug thereof, or a pharmaceutically acceptable salt of the same to said patient.

8. A method for treatment of hyperlipidemia or atherosclerosis in a patient in need, which comprises administering a therapeutically effective amount of the compound as set forth in any one of claims 1, 2, 3, 4 or 5, or a prodrug thereof, or a pharmaceutically acceptable salt of the same to said patient.

* * * * *